(12) United States Patent
Martinez et al.

(10) Patent No.: US 11,672,695 B2
(45) Date of Patent: Jun. 13, 2023

(54) CENTRAL NERVOUS SYSTEM LOCALIZED HYPOTHERMIA APPARATUS AND METHODS

(71) Applicant: Artivion, Inc., Kennesaw, GA (US)

(72) Inventors: Adam William Martinez, Kennesaw, GA (US); Rachel Candace Howell, Marietta, GA (US); Emily Renee Croft, Mableton, GA (US); Jeremy Gura, Peachtree City, GA (US); Alejandro A. Aviles, Kennesaw, GA (US)

(73) Assignee: ARTIVION, INC., Atlanta, GA (US)

( * ) Notice: Subject to any disclaimer, the term of this patent is extended or adjusted under 35 U.S.C. 154(b) by 972 days.

(21) Appl. No.: 16/361,566

(22) Filed: Mar. 22, 2019

(65) Prior Publication Data
US 2019/0290481 A1      Sep. 26, 2019

Related U.S. Application Data

(60) Provisional application No. 62/646,539, filed on Mar. 22, 2018.

(51) Int. Cl.
| | | |
|---|---|---|
| *A61F 7/12* | (2006.01) | |
| *A61M 25/00* | (2006.01) | |
| *A61M 27/00* | (2006.01) | |
| *A61M 39/22* | (2006.01) | |
| *A61F 7/00* | (2006.01) | |

(52) U.S. Cl.
CPC ............. *A61F 7/12* (2013.01); *A61M 25/007* (2013.01); *A61M 25/0026* (2013.01); *A61M 27/006* (2013.01); *A61M 39/22* (2013.01); *A61F 2007/0056* (2013.01); *A61F 2007/126* (2013.01); *A61M 2205/3334* (2013.01); *A61M 2205/366* (2013.01);
(Continued)

(58) Field of Classification Search
CPC ................ A61F 7/12; A61F 2007/0056; A61F 2007/126; A61F 2007/0054; A61M 25/0026; A61M 25/007
See application file for complete search history.

(56) References Cited

U.S. PATENT DOCUMENTS

| | | | |
|---|---|---|---|
| 3,662,598 A | 5/1972 | Spencer | |
| 3,985,601 A | 10/1976 | Panagrossi | |
| (Continued) | | | |

FOREIGN PATENT DOCUMENTS

| | | |
|---|---|---|
| DE | 102013104951 A1 | 11/2014 |
| EP | 1204368 A1 | 5/2002 |
| (Continued) | | |

OTHER PUBLICATIONS

Extended European Search Report issued in EP19772187.1, dated Dec. 9, 2021.
(Continued)

*Primary Examiner* — Laura A Bouchelle
(74) *Attorney, Agent, or Firm* — Meunier Carlin & Curfman IP Law

(57) ABSTRACT

Apparatus and methods for accomplishing fluid drainage and localized cooling of the central nervous system broadly encompassing an intrathecal catheter assembly accomplishing drainage and cooling, and a console apparatus that may contain control, cooling, and drainage subsystems, and use thereof.

19 Claims, 15 Drawing Sheets

(52) U.S. Cl.
CPC ............. *A61M 2205/3606* (2013.01); *A61M 2205/3673* (2013.01); *A61M 2210/1003* (2013.01)

(56) References Cited

U.S. PATENT DOCUMENTS

| | | | |
|---|---|---|---|
| 4,137,168 | A | 1/1979 | Perrot |
| 5,437,673 | A | 8/1995 | Baust |
| 6,036,654 | A | 3/2000 | Quinn |
| 6,074,565 | A | 6/2000 | Buckner |
| 6,129,701 | A | 10/2000 | Cimino |
| 6,149,676 | A | 11/2000 | Ginsburg |
| 6,231,595 | B1 | 5/2001 | Dobak, III |
| 6,235,048 | B1 | 5/2001 | Dobak, III |
| 6,289,600 | B1 | 9/2001 | Watts |
| 6,335,572 | B1 | 1/2002 | Uno |
| 6,419,643 | B1 | 7/2002 | Shimada et al. |
| 6,482,184 | B1 | 11/2002 | Christensen |
| 6,530,946 | B1 | 3/2003 | Noda |
| 6,620,188 | B1 | 9/2003 | Ginsburg |
| 6,626,902 | B1 | 9/2003 | Kucharczyk |
| 6,635,076 | B1 | 10/2003 | Ginsburg |
| 6,645,233 | B1 * | 11/2003 | Ayers .............. A61F 7/123 607/105 |
| 6,652,565 | B1 | 11/2003 | Shimada |
| 6,699,269 | B2 * | 3/2004 | Khanna ............. A61F 7/12 607/104 |
| 6,823,678 | B1 | 11/2004 | Li |
| 7,211,066 | B1 | 5/2007 | Merrill |
| 8,795,219 | B1 | 8/2014 | Al-Rashdan |
| 10,569,064 | B2 * | 2/2020 | Vase ............. A61M 25/0026 |
| 2001/0005791 | A1 | 6/2001 | Ginsburg |
| 2001/0007951 | A1 | 7/2001 | Dobak, III |
| 2001/0010011 | A1 | 7/2001 | Aliberto |
| 2001/0016764 | A1 | 8/2001 | Dobak, III |
| 2001/0044644 | A1 | 11/2001 | Keller |
| 2001/0047196 | A1 | 11/2001 | Ginsburg |
| 2002/0045852 | A1 | 4/2002 | Saab |
| 2002/0047007 | A1 | 4/2002 | Loyd |
| 2002/0161327 | A1 | 10/2002 | Kelley |
| 2002/0198578 | A1 | 12/2002 | Dobak, III |
| 2002/0198579 | A1 | 12/2002 | Khanna |
| 2003/0014016 | A1 | 1/2003 | Purdy |
| 2003/0069621 | A1 | 4/2003 | Kushnir |
| 2003/0130651 | A1 | 7/2003 | Lennox |
| 2003/0144623 | A1 | 7/2003 | Heath |
| 2003/0216710 | A1 | 11/2003 | Hurt |
| 2003/0236489 | A1 | 12/2003 | Jacobson |
| 2004/0010208 | A1 | 1/2004 | Ayad |
| 2004/0019312 | A1 | 1/2004 | Childers |
| 2004/0024347 | A1 | 2/2004 | Wilson |
| 2004/0024358 | A1 | 2/2004 | Meythaler |
| 2004/0102827 | A1 | 5/2004 | Werneth |
| 2004/0138728 | A1 | 7/2004 | Wong |
| 2004/0177623 | A1 | 9/2004 | Zelissen |
| 2004/0211189 | A1 | 10/2004 | Arnold |
| 2004/0225341 | A1 | 11/2004 | Schock |
| 2004/0267339 | A1 | 12/2004 | Yon |
| 2005/0177212 | A1 | 8/2005 | Njemanze |
| 2005/0192548 | A1 | 9/2005 | Dolliver |
| 2005/0222652 | A1 | 10/2005 | Mori |
| 2005/0273144 | A1 | 12/2005 | Lennox |
| 2006/0053805 | A1 | 3/2006 | Flinner |
| 2006/0089689 | A1 | 4/2006 | Hennemann |
| 2006/0167438 | A1 | 7/2006 | Kalser |
| 2006/0171506 | A1 | 8/2006 | Lovoi |
| 2006/0175543 | A1 * | 8/2006 | Elefteriades ............. A61F 7/12 250/231.16 |
| 2006/0184098 | A1 * | 8/2006 | Barnitz ............. A61M 25/007 604/43 |
| 2007/0038171 | A1 * | 2/2007 | Mayer ............. A61M 27/006 604/9 |
| 2007/0050002 | A1 | 3/2007 | Elefteriades |
| 2007/0058155 | A1 | 3/2007 | Booker |
| 2007/0224063 | A1 | 9/2007 | Postma |
| 2007/0245765 | A1 | 10/2007 | Casher |
| 2008/0024992 | A1 | 1/2008 | Pflueger |
| 2008/0031773 | A1 | 2/2008 | Eccleston |
| 2008/0033400 | A1 | 2/2008 | Holper |
| 2008/0044473 | A1 | 2/2008 | Radojicic |
| 2008/0077088 | A1 | 3/2008 | Collins |
| 2008/0077202 | A1 | 3/2008 | Levinson |
| 2008/0200877 | A1 | 8/2008 | Panotopoulos |
| 2008/0306425 | A1 | 12/2008 | Al-Rashdan |
| 2009/0018504 | A1 | 1/2009 | Pile-Spellman |
| 2009/0054824 | A1 | 2/2009 | Melsheimer |
| 2009/0076573 | A1 | 3/2009 | Burnett |
| 2009/0099482 | A1 | 4/2009 | Furuhata |
| 2009/0287281 | A1 | 11/2009 | Munson |
| 2010/0082012 | A1 | 4/2010 | Hattangadi |
| 2010/0217361 | A1 | 8/2010 | Kulstad |
| 2010/0305492 | A1 | 12/2010 | Lad |
| 2010/0324635 | A1 | 12/2010 | Kreck |
| 2011/0208278 | A1 | 8/2011 | MacHold |
| 2011/0276115 | A1 | 11/2011 | Merrill |
| 2012/0017999 | A1 | 1/2012 | Velschow |
| 2012/0018136 | A1 | 1/2012 | Dunwoody |
| 2012/0191069 | A1 | 7/2012 | Thomas |
| 2012/0260671 | A1 | 10/2012 | Damren |
| 2012/0283676 | A1 | 11/2012 | Hoffman et al. |
| 2012/0302938 | A1 | 11/2012 | Browd |
| 2012/0302995 | A1 | 11/2012 | Hochareon |
| 2013/0030411 | A1 | 1/2013 | Kreck |
| 2013/0103126 | A1 | 4/2013 | Harikrishna |
| 2013/0104953 | A1 | 5/2013 | Poliquin |
| 2013/0287613 | A1 | 10/2013 | Gould |
| 2014/0031631 | A1 | 1/2014 | Hall et al. |
| 2014/0240406 | A1 | 8/2014 | Lacaze |
| 2015/0080952 | A1 | 3/2015 | Drnek |
| 2015/0204733 | A1 | 7/2015 | Newell |
| 2015/0238354 | A1 | 8/2015 | Rajguru |
| 2015/0359996 | A1 | 12/2015 | Arora |
| 2016/0131127 | A1 | 5/2016 | Hendricks |
| 2016/0331282 | A1 | 11/2016 | Satish et al. |
| 2018/0104391 | A1 | 4/2018 | Luxon |
| 2019/0105476 | A1 * | 4/2019 | Turtz ............. A61B 5/0031 |

FOREIGN PATENT DOCUMENTS

| | | | |
|---|---|---|---|
| EP | 1641503 | A2 | 4/2006 |
| JP | S5343997 | A | 4/1978 |
| JP | H01204674 | A | 8/1989 |
| WO | WO2001012061 | A1 | 2/2001 |
| WO | WO-2005084125 | A2 * | 9/2005 ............. A61M 1/00 |
| WO | 2008079202 | A1 | 7/2008 |
| WO | WO2017062606 | A1 | 4/2017 |

OTHER PUBLICATIONS

3M Health Care, Infection Prevention Division, 3M Ranger blood & fluid warming systems: Smart, intuitive dry heat technology solution, 2015.
3M Health Care, Infection Prevention Division, "3M Ranger Blood/Fluid Warming Unit, Model 245, Service Manual".
Attune Medical, "ensoETM Esophageal Temperature Management, A simple solution for a complex therapy".
Bard Medical, "Arctic Sun 5000 Temperature Management System", 2012.
Irras, "Introducing IRRAflow", https://irras.com/product/introducing-irraflow/# accessed Apr. 16, 2019.
Moller Medical, "Liquogard", https://www.moeller-medical.com/end-use/liquoguardr.html accessed Apr. 16, 2019.
Novocor Medical Systems, Inc., Department of Health and Human Services 510(k) premarket notification for Hypocore thermal regulating system, May 20, 2016.
Seiratherm GMBH, Department of Health and Human Services 510(k) premarket notification for tempedy 5000 thermal regulating system, Sep. 15, 2016.
Stryker Medical, "Medi-Temp D25000 Series Blood/Fluid Warming Set Instructions for Use".
Gaymar Industries, Inc., "Medi-Temp II FW400/FW401/REF FW403 Blood/Fluid Warmer Service Manual", Dec. 2000.

(56) References Cited

OTHER PUBLICATIONS

Medtronic, "Duet External Drainage and Monitoring System", https://www.medtronic.com/us-en/healthcare-professionals/products/neurological/critical-care/duet-external-drainage-monitoring-system.html accessed Sep. 26, 2019.
3M, "Ranger blood and fluid warming systems" https://www.3m.com/3M/en_US/company-us/all-3m-products/~/All-3M-Products/Health-Care/Surgical-Safety-Solutions/Fluid-Warming/?N=5002385+8707795+8710775+8711017+8711100+3294857497&rt=r3, accessed Sep. 26, 2019.
Integra Lifesciences Corporation, "AccuDrain External CSF Drainage Management System", https://www.integralife.com/accudrain-external-csf-drainage-management-system/product/neurocritical-care-evd-drains-accudrain-accudrain-external-csf-drainage-management-system, accessed Sep. 26, 2019.
Zoll Medical Corporation, "Thermogard XP Temperature Management System", https://www.zoll.com/medical-products/temperature-management-systems/thermogard-xp/, accessed Sep. 26, 2019.
International Search Report and Written Opinion for International Application No. PCT/US2019/023556 dated Jun. 14, 2019.
International Preliminary Report on Patentability for International Application No. PCT/US2019/023556 dated Oct. 1, 2020.
English translation of Japanese Office Action issued in JP 2021-500502, dated Jan. 17, 2023.

\* cited by examiner

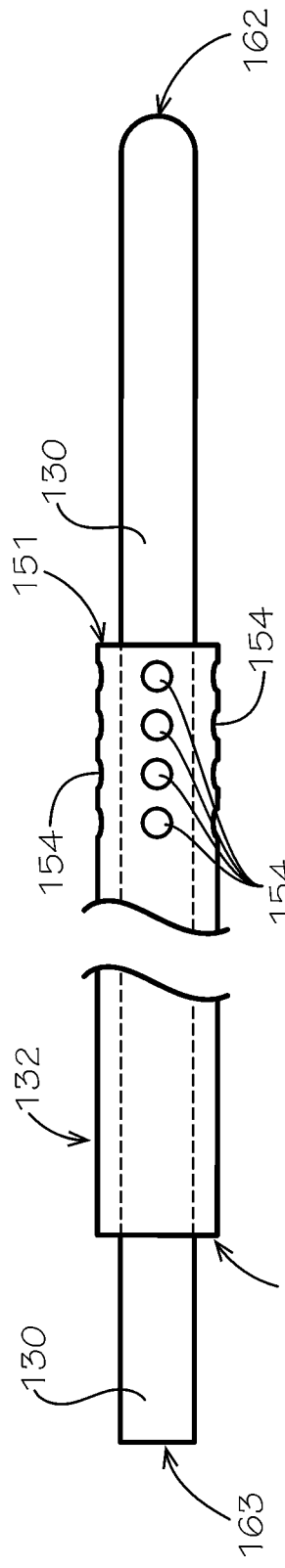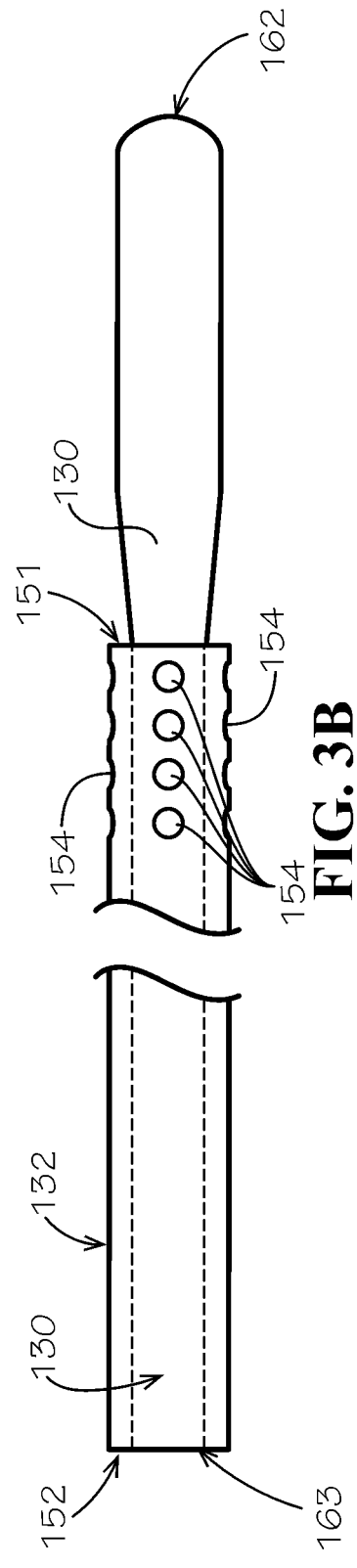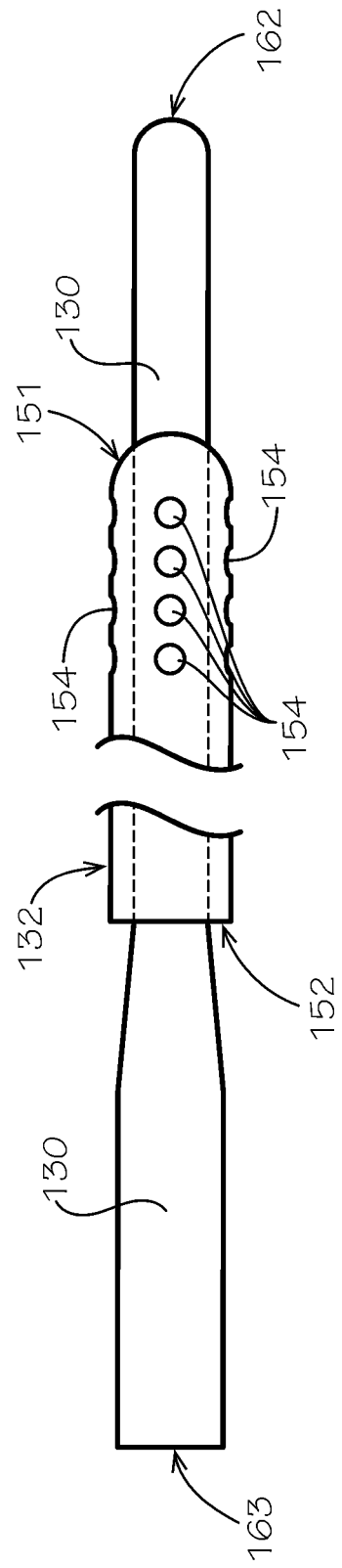

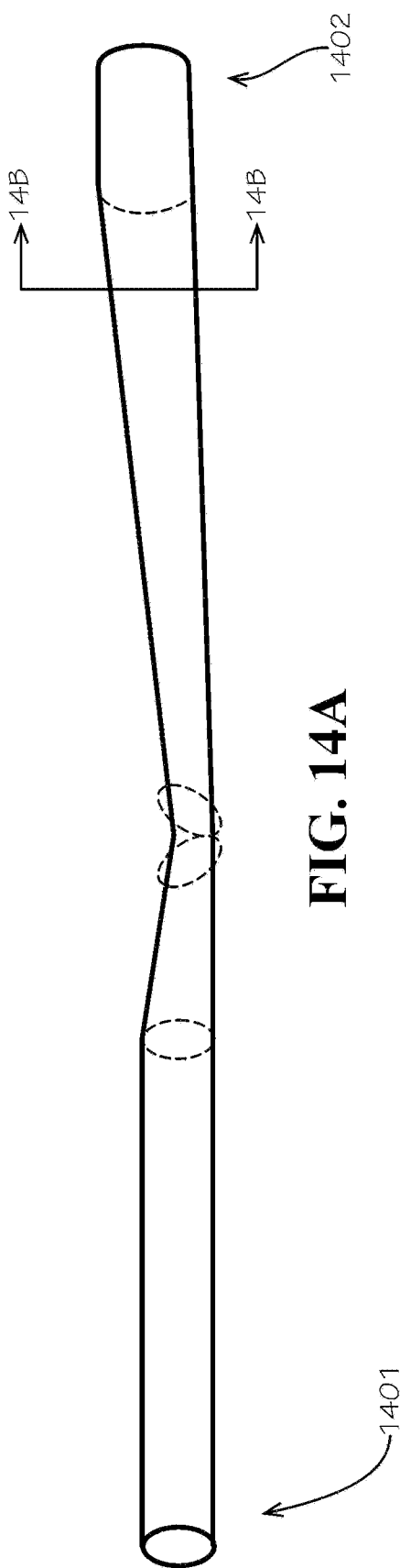 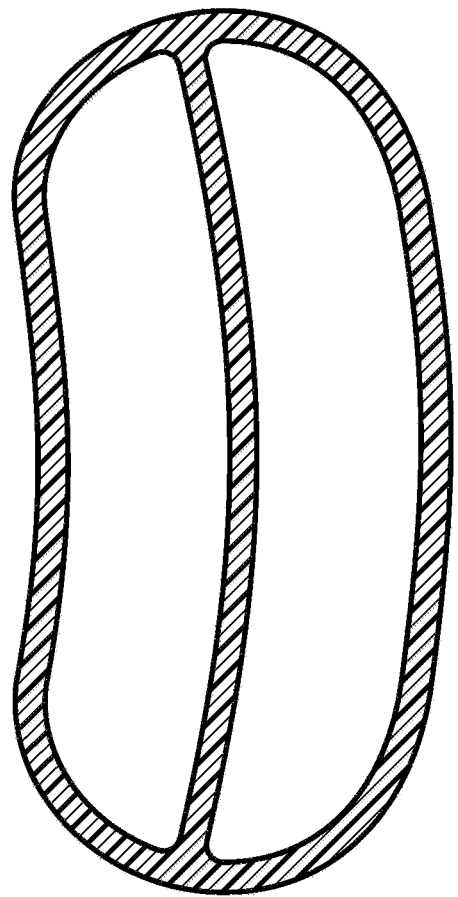
FIG. 14A
FIG. 14B

CENTRAL NERVOUS SYSTEM LOCALIZED HYPOTHERMIA APPARATUS AND METHODS

RELATED APPLICATIONS

This application claims priority under 35 U.S.C. § 119 to U.S. Provisional Patent Application No. 62/646,539, filed Mar. 22, 2018, and titled "Central Nervous System Localized Hypothermia Apparatus and Methods," the entire contents of which are incorporated herein by reference.

TECHNICAL FIELD

Embodiments disclosed herein are generally related to cooling and drainage systems for the central nervous system (CNS), and more particularly, to apparatuses and methods for creating localized hypothermia in the cerebral and spinal spaces.

BACKGROUND

In general, the human brain and spinal cord are maintained at a constant temperature of approximately 37 to 38 degrees Celsius. Mild hypothermia occurs when the body temperature is 33 to 35 degrees Celsius, moderate hypothermia between the temperatures of 28 to 32 degrees Celsius, and severe hypothermia in the temperature range of 24 to 28 degrees Celsius.

Inducement of localized CNS hypothermia has been shown to provide protection from cerebral and spinal cord injury resulting from ischemia, hypoxia, or trauma. Ischemia occurs when blood flow through arteries is reduced, decreasing the amount of oxygen available in the blood stream. Ischemia may be caused by atherosclerosis, blood clots, cardiac arrest, stroke, head or spinal cord injury, aneurysm surgery, cardiac surgery, aortic surgery, or carotid surgery. Hypothermia has been shown to provide benefits in these cases, for example: reducing cerebral glucose and oxygen metabolism and decreasing lactate content following injury; preventing disruption of the blood brain barrier and consequently reducing cerebral edema; reducing endogenously toxic neurotransmitters like glutamate, glycine, aspartate, acetylcholine, and norepinephrine into the brain after injury; inhibiting excessive calcium entry and intracellular calcium overload into neurons; protecting membrane structural proteins like microtubule-associated protein-2; and preventing diffuse axonal injury following brain trauma. Hypothermia is also effective in reducing increased intracranial pressure and intrathecal pressure from cerebral and spinal cord swelling respectively. Induced hypothermia can significantly mitigate the risk of ischemic injury in certain vascular surgical procedures such as those involving both open and endovascular thoracoabdominal aortic aneurysm (TAAA). Such procedures risk injury to the spinal cord that in severe cases may result in paraplegia and paraparesis, so induced hypothermic procedures such as hypothermic circulatory arrest or hypothermic circulatory arrest with brain and lower body perfusion are sometimes used.

Certain injuries and medical procedures may result in an increase of intracranial pressure or intrathecal pressure due to, for example, cerebral or spinal cord swelling. Untreated, these pressure increases can result in head ache, blurred vision, lethargy, or problems with motor control and may result in complications that can include seizures, stroke, neurological damage, or even death. Traditionally, the standard of care for alleviating increased intracranial pressure or increased intrathecal pressure has been through the use of a lumbar drainage catheter without the use of localized or systemic cooling.

Traditionally, cooling of the brain and spinal cord has been accomplished through whole body cooling with use of a cooling blanket, immersing the patient in ice, or cooling the blood through a cardiopulmonary bypass machine. However, systemic hypothermia is generally of limited use because of the significant side effects that may occur including infection, cardiac arrhythmias, coagulopathy, renal failure, as well as rewarming shock. In order to avoid these complications, the degree and duration of induced systemic hypothermia administered by clinicians has been shortened, limiting its effectiveness.

Previous attempts to induce localized brain or spinal cord hypothermia, including the use of arterial vessel or blood supply cooling, or external cooling helmets, have had limited success. Several catheters have been developed to induce localized hypothermia by inserting them into the bloodstream. More recently, catheters have been developed that can be inserted into the arterial vessels to the brain to induce selective brain hypothermia. The small vessel size severely limits the size of catheters used and the level of cooling that can be achieved. Cooling is further limited by the inability to cool all the four major arterial vessels supplying blood to the brain simultaneously. In addition to the lack of efficacy associated with these intra-arterial cooling methods, these devices increase the risk of ischemic and thromboembolic stroke by either impairing the blood flow to the brain and potentially dislodging clots that can develop in intra-arterial catheters. Additionally, the relatively quick flow of cooled blood through the brain or in the vicinity of the spinal column tends to degrade the cooling effect from a cooled blood supply, whereas a catheter placed in a more confined fluid environment, e.g., the intrathecal space, will result in more effective localized cooling. External cooling helmets have limited effectiveness since the blood to the cooled scalp does not circulate into the brain. This, combined with the insulating effect of the skull, degrades the hypothermic effect to the brain.

Many of the patients with the conditions or injuries described above also require management of cerebrospinal fluid (CSF) pressure. During procedures that may lead to an increase in the intrathecal pressure, which negatively impacts spinal cord perfusion, CSF pressure is managed typically by draining a certain volume of fluid in a given period, e.g., 20 mL/hour, a rate that is typically determined through empirical clinical data. For these procedures, a CSF drain is used to maintain pressure within acceptable ranges by reducing the CSF fluid volume in the intrathecal space.

Reduction of intrathecal pressure (ITP), including via CSF drainage, can increase the perfusion pressure (a byproduct of the pressure differential between the mean arterial pressure (MAP) and the ITP) which can improve the perfusion of nutrients from the blood stream into the neural tissues. Lowering and maintaining the ITP allows clinicians to preserve the pressure differential between the ITP and the MAP to promote the perfusion of nutrients in adjacent collateral networks into the surrounding tissues.

Placement of CSF drains and other procedures may necessarily result in a penetration of the spinal dura to access intrathecal or subdural spaces. Upon completion of the procedure or treatment plan, the penetrating devices are removed from the patient, leaving behind an opening in the dura through which CSF may continue to drain. Upon removal, the dura is capable of "self-sealing" and, depending on the size and geometry of the dural penetration, preventing any further drainage of CSF. Dural penetrations that are not capable of self-sealing may be sealed, for example through the use of dural sealants or a blood patch using the natural clotting factors of a patient's blood. It is therefore desirable to minimize the size of any dural penetration to reduce or eliminate the need for post-operative intervention to prevent additional unintended CSF drainage.

Accordingly, there is a need for improved systems and methods of providing cooling and drainage for the central nervous system, and more particularly, for improved apparatuses and methods for creating localized hypothermia in the cerebral and spinal spaces that minimize the size of the dural opening.

SUMMARY

The embodiments described herein generally encompass an apparatus and reference methods for accomplishing fluid drainage and localized cooling of the central nervous system. The embodiments broadly encompass an intrathecal catheter assembly accomplishing drainage and cooling, and a console apparatus that may contain control, cooling, and drainage subsystems.

BRIEF DESCRIPTION OF THE DRAWINGS

For a more complete understanding of the present disclosure and certain features thereof, reference is now made to the following description, in conjunction with the accompanying figures briefly described as follows:

FIG. 3A is a partial side view of a coaxial cooling and drainage catheter assembly in accordance with one example embodiment of the disclosure.

FIG. 3B is a partial side view of another coaxial cooling and drainage catheter assembly in accordance with one example embodiment of the disclosure.

FIG. 3C is a partial side view of another coaxial cooling and drainage catheter assembly in accordance with one example embodiment of the disclosure.

FIG. 14A illustrates a variable cross section catheter assembly in accordance with one example embodiment of the disclosure.

FIG. 14B is a cross sectional view of a portion of the variable cross section catheter assembly of FIG. 14A.

DETAILED DESCRIPTION

Example embodiments of the invention now will be described more fully hereinafter with reference to the accompanying drawings, in which example embodiments are shown. This invention may, however, be embodied in many different forms and should not be construed as limited to the exemplary embodiments set forth herein; rather, these embodiments are provided so that this disclosure will be thorough and complete, and will fully convey the scope of the invention to those skilled in the art. Throughout this description, certain dimensions are listed in accordance with the French scale, also referred to the French gauge scale, the unit of measure associated with catheter dimensions. For reference, a round catheter of 1 French ("1 Fr") has an external diameter of ⅓ mm.

Certain dimensions and features of example cooling and drainage systems are described herein using the term "about." As used herein, the term "about" indicates that each of the described dimensions is not a strict boundary or parameter and does not exclude functionally similar variations therefrom. Unless context or the description indicates otherwise, the use of the term "about" in connection with a numerical parameter indicates that the numerical parameter includes variations that, using mathematical and industrial principles accepted in the art (e.g., rounding, measurement or other systematic errors, manufacturing tolerances, etc.), would not vary the least significant digit.

The invention provides a method and apparatus for generating localized hypothermia to the brain and/or the spinal cord for injury prevention. As described more fully below, the spinal cooling and drainage system 100 includes a console 110, for housing the various subassemblies and controls, a catheter assembly 112, for insertion into a patient, and a tubing set 114, for fluidically connecting the console 110 and the catheter assembly 112.

Figure 1:
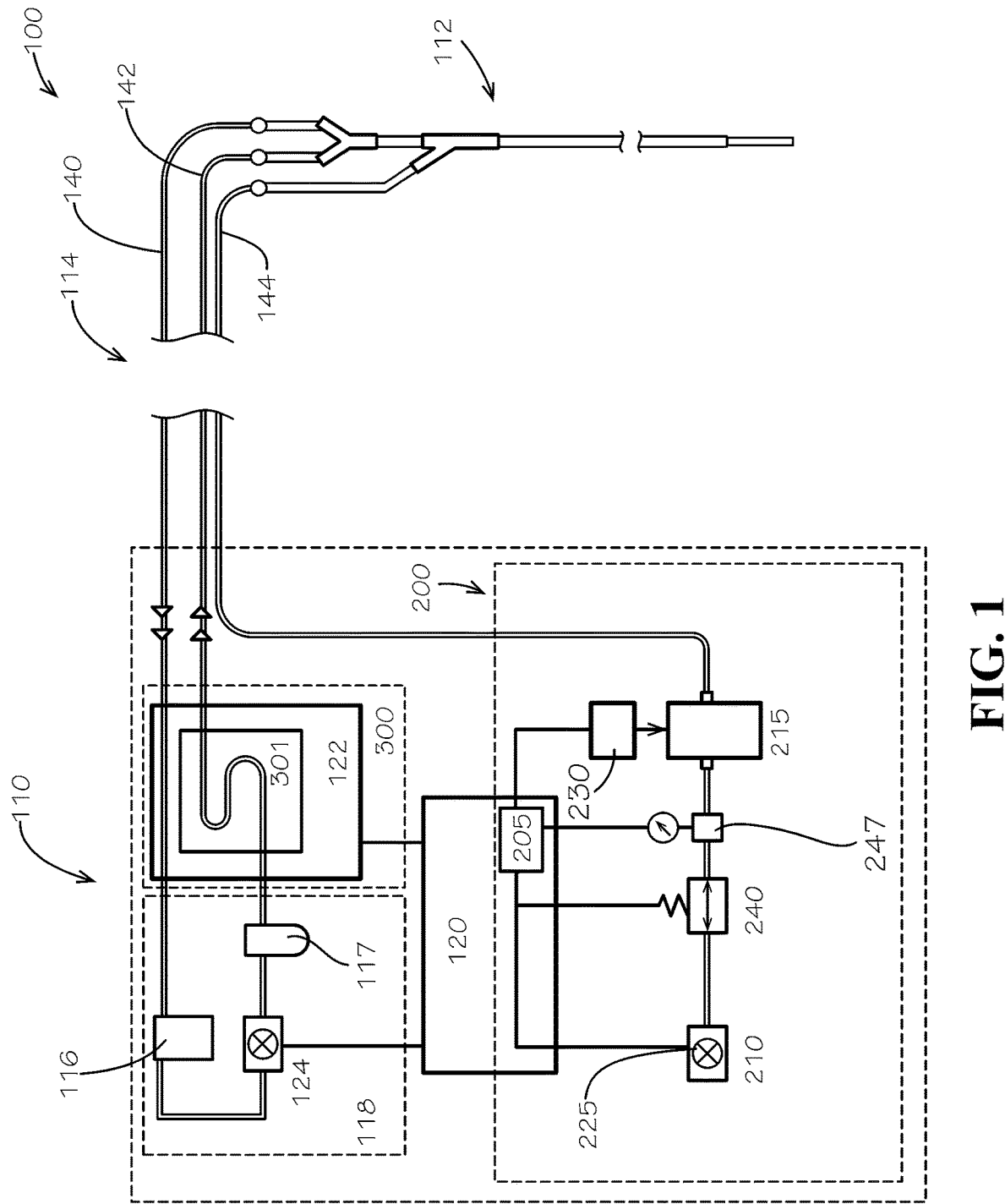
FIG. 1 is a functional block diagram of a combined cooling and drainage system in accordance with one example embodiment of the disclosure.

FIG. 1 provides a schematic overview of one embodiment of the cooling and drainage system 100 that may be used to induce localized hypothermia in a patient's brain or spinal column. The console 110 includes a cooling system 300 with a circulation system 118, and a control system 120, the control system 120 being operatively connected to, and configured to control, the other components of the console 110. The cooling system 300 may include a chiller 122, as described in more detail below, and a coolant, which circulates between the cooling system 300, the tubing set 114, and the catheter assembly 112. The circulation system 118 may include a coolant pump 124 or other means for circulating the coolant through the components of the cooling and drainage system 100 and tubing to route the coolant as necessary. Circulation system 118 may also include coolant reservoir 116 and air trap 117. The coolant is typically a benign, low-viscosity fluid such as saline (e.g., 0.9% NaCl). The circulation system 118 can be configured to control the flow of coolant within the system by varying the flow rate or modulating flow on and off. In use, circulation of coolant through the cooling circuit, from the distal tip of the cooling catheter to the heat exchanger of the cooling system, allows for the transfer of heat from the site of implantation within the patient to the heat exchanger in the console, allowing for the localized cooling of the implantation site and surrounding areas.

The cooling and drainage system 100 includes a catheter assembly 112 as shown in FIG. 1, and as illustrated in more detail in FIGS. 2-8 and described below. Generally, the catheter assembly 112 is configured for minimally-invasive insertion into a patient to allow for localized cooling by circulating a coolant through the catheter assembly 112 after placement. By circulating a cooled fluid through the catheter assembly 112, the system can cool surrounding fluid and tissue and, with sufficient cooling capacity, induce localized hypothermia as discussed above. During use, the catheter assembly 112 is inserted the dura at least partially into the intrathecal space, the fluid-filled space between the thin layers of tissue that cover the brain and spinal cord. In this position, the catheter assembly 112 is at least in partial contact with cerebrospinal fluid (CSF) for locally cooling the spine. Upon completion of the procedure or treatment plan, the catheter assembly 112 is removed from the patient. Upon removal, the dura is capable of "self-sealing" and, depending on the size and geometry of the dural penetration, preventing any further drainage of CSF. Dural penetrations that are not capable of self-sealing may be sealed, for example, through the use of dural sealants or through a blood patch using the natural clotting factors of a patient's blood. Accordingly, it is desirable to minimize the size of any dural penetration to reduce or eliminate the need for post-operative intervention to prevent additional unintended CSF drainage.

As referenced above, certain injuries and procedures may result in an increase of intracranial pressure or intrathecal pressure due to, for example, cerebral swelling. Untreated, these pressure increases can result in head ache, blurred vision, lethargy, or problems with motor control and may result in complications that can include seizures, stroke, neurological damage, or even death. Accordingly, in addition to the use of localized hypothermia to reduce the metabolic rate of CNS tissues, it may also be beneficial or necessary to also allow for drainage of extra CSF to maintain desired pressure levels under certain circumstances.

Figure 2:
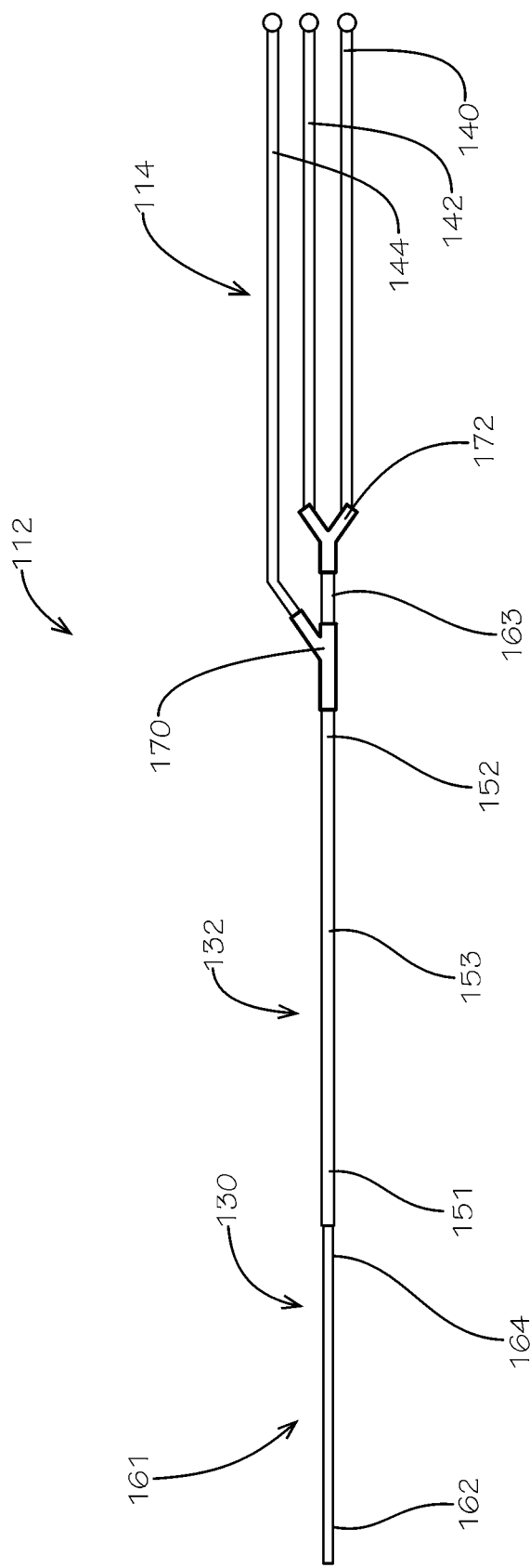
FIG. 2 is a top perspective view of a coaxial cooling and drainage catheter assembly in accordance with one example embodiment of the disclosure.

Accordingly, the catheter assembly 112 is also configured to allow for CSF drainage. As shown in FIG. 2, and described more fully below, one embodiment of the catheter assembly 112 includes both a cooling catheter 130 and a drainage catheter 132. In some embodiments, the cooling catheter 130 may be removably inserted through a central lumen 134 of the drainage catheter 132 (as shown in FIG. 3) and be configured to allow CSF to flow in the space between the outer surface of the cooling catheter 130 and the inner surface of the central lumen of the drainage catheter 132. In other embodiments, as shown in FIGS. 15-18, the catheter assembly 112 may include a single, multi-lumen catheter 900 that includes at least a coolant inlet lumen 902, a coolant outlet lumen 904, and a drainage lumen 906. Variations on the catheter assembly 112 configuration may be utilized to allow for different cooling, drainage, and self-healing characteristics.

As shown in FIG. 1, the cooling and drainage system 100 may include a tubing set 114 for fluidically connecting the console 110 and the catheter assembly 112. As explained in more detail below, the tubing set 114 may include a first fluid pathway 140 for coolant flowing to the catheter assembly 112, a first fluid pathway 142 for coolant flowing from the catheter assembly 112, and a third fluid pathway 144 to allow the drainage of cerebral spinal fluid (CSF) away from the catheter assembly 112. In some exemplary embodiments, each fluid pathway is an independent piece of tubing with individual connectors, resulting in three separate tubing pieces, while in other exemplary embodiments two or more fluid pathways may be secured together to create a tubing sub-assembly. In yet another exemplary embodiment, the tubing pathways may consist of three fluid pathways in a single multi-lumen tube or hose. As may be appreciated by one skilled in the art, additional fluid pathways or connections may be included in the tubing set 114 and catheter assembly 112 to, for example, allow for aspiration, to allow for the injection of therapeutic agents, to allow for the injection of contrast agents, or to allow for the passage of additional surgical and diagnostic tools like guidewires. Alternatively, some embodiments may be configured to provide communicative connectivity between the console 110 and pressure or temperature sensors inserted into the patient, or allow for the manipulation of the catheter assembly 112, for example, by steering the catheter assembly via steerable guidewire or by manipulating the pressure or fluid flow within the catheter assembly to cause a change in catheter geometry.

As noted above, the console 110 may include a control system 120 that is operatively connected to, and configured to control, the components of the console 110. The control system 120 can receive inputs, either from a user or other system components, and control the overall operation of the drainage and cooling system 300, including the operation of the cooling system 300 and the circulation system 118. As would be appreciated by one of skill in the art, the control system 120 can be based on any of the well-known types of industrial controllers, including programmable logic controllers (PLCs), personal computers, single-board computers such as the Raspberry Pi, or a custom-built control solution. In some exemplary embodiments, and as is explained more fully below, the control system 120 is operatively connected to sensors within the system, such as pressure or vacuum sensors, temperature sensors, or flow sensors that may provide operative feedback as an input to the system operation or for display to an end user. The control system 120 also includes various human machine interface components, such as touch screens or other physical inputs, switches, or buttons, that are configured to allow a user to control the operation of the system.

FIGS. 2 and 3A-3C illustrate exemplary catheter assemblies in accordance with one embodiment of the disclosure. In one example, the catheter assembly 112 may include both a cooling catheter 130 and a drainage catheter 132. As shown, the drainage catheter 132 can have a generally cylindrical body with a distal end 151, a proximal end 152, an outer surface 153, and a central lumen 134 passing from the distal end 151 to the proximal end 152. Also as shown, the cooling catheter 130 can have an elongate body 161 with a distal end 162, a proximal end 163, and an outer surface 164. As shown in FIGS. 3A-3C, the catheter assembly 112 may include atraumatic geometries at the distal end (or leading edges) of the catheters. For example, as shown in FIGS. 3A-3C, the distal end 162 of the cooling catheter 130 may include a rounded end to prevent or reduce the potential for damage to the spinal cord and dura. Alternatively, the tip may incorporate a bullet, angled, conical, chamfered, or tapered shape. As shown in FIG. 3C, the drainage catheter may have similar leading-edge geometries for the same reasons.

In some circumstances, it may be desirable to remove the cooling catheter 130 from the patient after insertion, while leaving the drainage catheter 132 in place. Accordingly, the cooling catheter 130 and the drainage catheter 132 can be configured so that the cooling catheter 130 is removably insertable into the drainage catheter 132 and be configured to allow CSF to flow in the space between the outer surface of the cooling catheter 130 and the inner surface of the central lumen of the drainage catheter 132 as shown in FIG. 3A Similarly, the cooling catheter 130 and drainage catheter 132 may come preassembled and, in that case, the cooling catheter 130 may be selectively removable from the drainage catheter 132.

FIG. 3B illustrates one example of the catheter assembly 112 that includes a cooling catheter 130 with a distal end 162 that includes a larger diameter than the proximal end 163. As shown, the cooling catheter 130 may expand after exiting the drainage catheter 132 until both the cooling catheter 130 and the drainage catheter 132 have the same outer diameter. In one example embodiment, an about 4 Fr outer diameter cooling catheter 130 extends through the central lumen 134 of a drainage catheter 132 with an about 5 Fr outer diameter, once the cooling catheter 130 extends beyond the end of the drainage catheter 132, it expands until the cooling catheter 130 has an outer diameter of about 5 Fr. The increased diameter of the distal end 162 of the cooling catheter 130 can increase the surface area in contact with the surrounding fluid and tissue, increasing the heat transfer properties, or may allow more space for the coolant to recirculate through the tip. FIG. 3B also illustrates an example where the drainage catheter 132 extends proximally, covering substantially all of the proximal end 163 of the cooling catheter 130, allowing for different configurations of mating assemblies and tubing sets to be used to adapt the catheter assembly 112 to the tubing set 114.

FIG. 3C illustrates another example of the catheter assembly 112 where the distal end 162 of the cooling catheter 130 may have a smaller profile or cross section for insertion into the intrathecal space, while the proximal end 163 may have a larger diameter (as shown) or otherwise different cross section. These types of changes may, for example, help make the catheter assembly 112 more durable, improve connectivity to the tubing set 114, ease manufacturing, or provide other benefits. The examples shown in FIGS. 3A-3C are exemplary and other geometric combinations are contemplated within the scope of this disclosure.

Figure 4A:
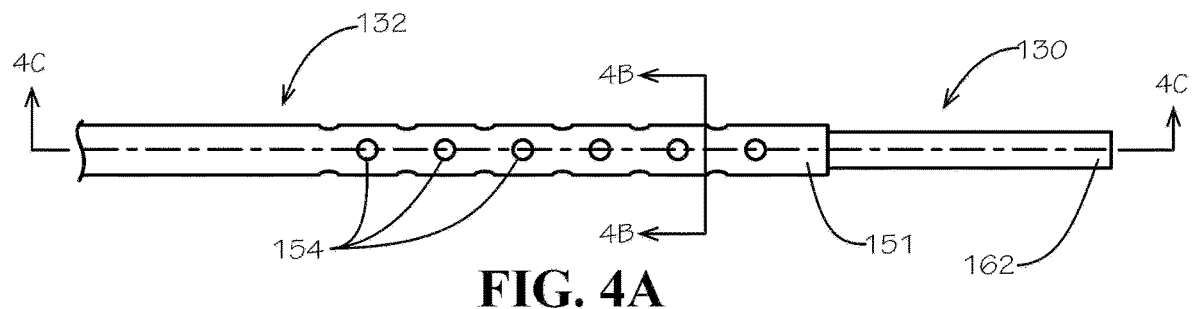
FIG. 4A is a partial side view of a coaxial cooling and drainage catheter assembly in accordance with one example embodiment of the disclosure.
Figure 4B:
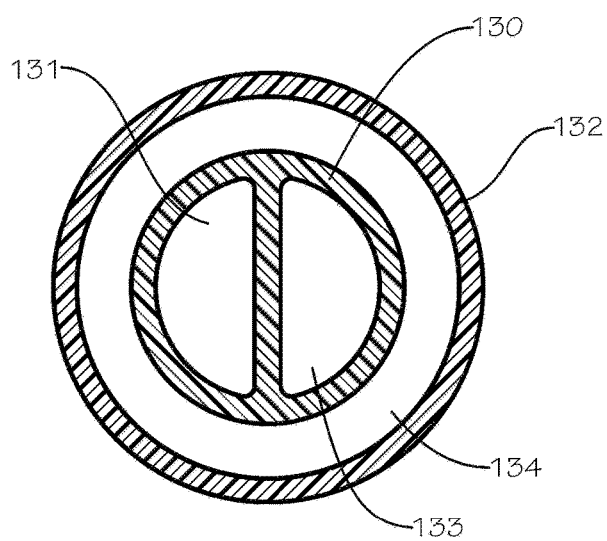
FIG. 4B is a sectional view of the cooling and drainage catheter assembly of FIG. 4A.
Figure 4C:
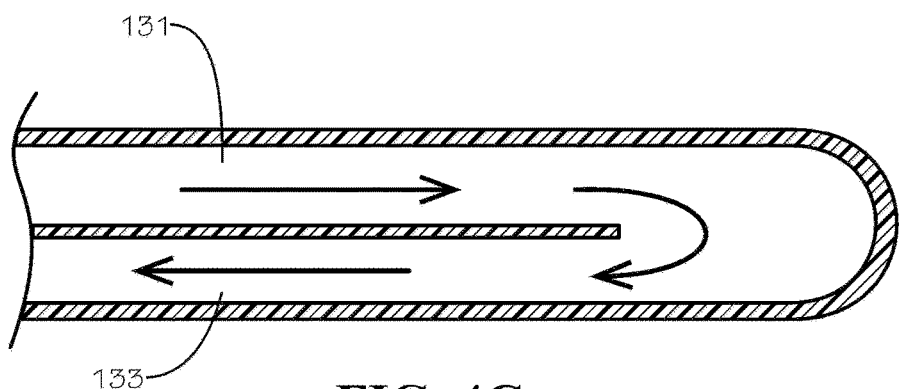
FIG. 4C is a partial sectional view of the distal tip of the cooling and drainage catheter assembly of FIG. 4A.

FIG. 4A shows a partial view of the distal end of the catheter assembly 112 in accordance with one embodiment of the present disclosure. FIG. 4B shows a section view of the catheter assembly 112 shown in FIG. 4A along line "4B." As shown in FIG. 4B, the drainage catheter 132 is coaxially mounted over the cooling catheter 130. The open space in the central lumen 134 of the drainage catheter, the space between the outer wall of the cooling catheter and the inner wall of the drainage catheter, provides a pathway for CSF to flow. FIG. 4B also shows an exemplary embodiment of the cooling catheter 130 with two equal sized inner lumens, an inlet lumen 131, through which coolant flows towards the distal tip 162 of the cooling catheter, and an outlet lumen 133, through which coolant flows out of the cooling catheter 130 towards the console 110. As shown in FIG. 4C, which is a section view of the catheter assembly 112 shown in FIG. 4A along line "4C," the inlet lumen 131 and the outlet lumen 133 are fluidically connected towards the distal end 162 of the cooling catheter 130 allowing the coolant to circulate in and back out the proximal end 163 of the cooling catheter 130.

In these multi-piece embodiments, the catheter assembly 112 may include a mating assembly 170 configured to secure the drainage catheter 132 to the cooling catheter 130 and create a seal so that drainage fluid flowing through the central lumen 134 of the drainage catheter 132 can be directed to the third fluid pathway 144 of the tubing set 114. Current intrathecal catheter kits commonly require the end user to attach the mating assembly to the catheter prior to or during placement which can be cumbersome and prone to error. By pre-attaching this the mating assembly to the drainage catheter the ease of use is improved and the potential for damage or improper assembly is removed. Similarly, the cooling catheter 130 may include or be adapted to use a Y-fitting 172 to fluidically connect the inlet lumen 131 to the first fluid pathway 140, and the outlet lumen 133 to the second fluid pathway 142 of the tubing set 114.

Figure 5:
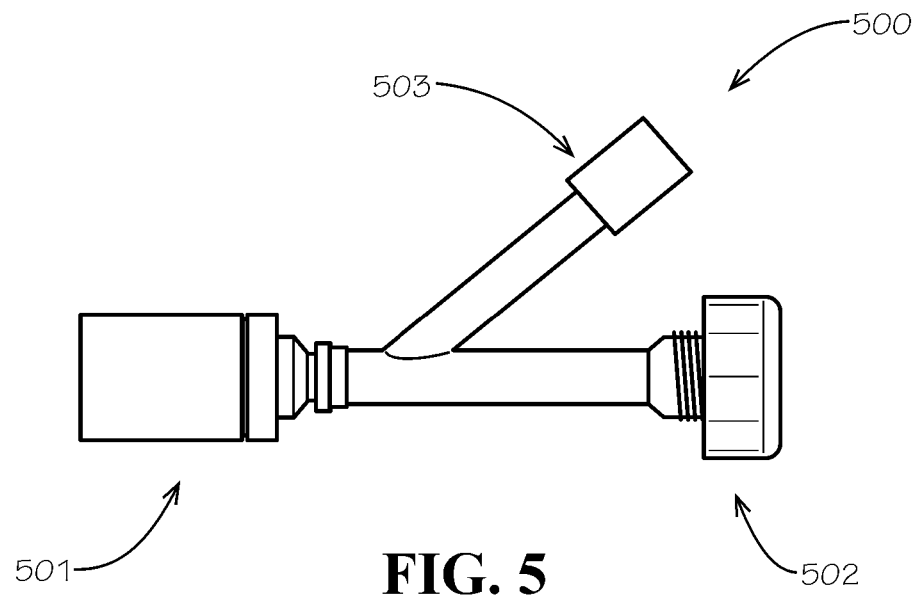
FIG. 5 is a top perspective view of a mating assembly in accordance with one example embodiment of the disclosure.

In one example embodiment, illustrated in FIG. 5 the mating assembly 500 uses a Tuohy Borst hemostasis valve (e.g., Qosina Part No. 80303) where a first end 501 can selectively sealingly couple to the outer surface 153 of the drainage catheter 132 and an opposite second end 502 can selectively sealingly couple to the outer surface 164 of the cooling catheter 130. As shown in FIG. 5, this assembly includes a drainage port 503, when the first end 501 is sealingly coupled to the drainage catheter 132 and the second end 502 is sealingly coupled to the cooling catheter 130, any fluid flowing out the proximal end 152 of the drainage catheter 132 can flow out the drainage port 503. As would be understood by one of skill in the art, the mating assembly may utilize other securement methods including those illustrated in FIGS. 6-8, including features such as press-fit rubber stoppers, shrink tubing, or clamps to create a seal around the cooling catheter.

Figure 6:
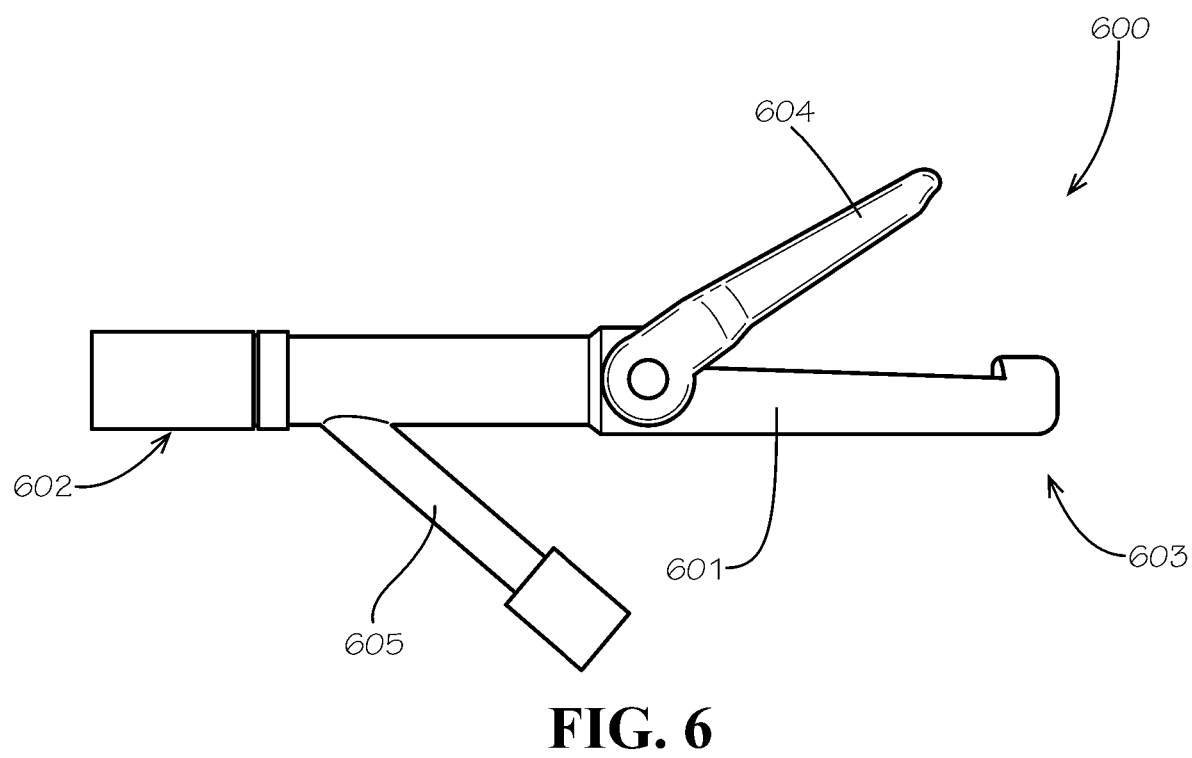
FIG. 6 is a top view of another mating assembly in accordance with one example embodiment of the disclosure.

In another exemplary embodiment, illustrated in FIG. 6, the mating assembly 600 includes a generally elongated body 601, an attachment end 602, a pass-through end 603, a clamp 604, and a drainage port 605 extending outward from a point along elongated body 601. The attachment end 602 is configured to allow for insertion of and selective sealed attachment to the proximal end 152 of the drainage catheter 132. When inserted, the drainage catheter 132 extends partially into the body 601 of the mating assembly 600, and the cooling catheter 130, which is mounted coaxially inside of the drainage catheter 132, extends through the length of the body 601, extending out the pass-through end 603 of the mating assembly 600. As shown in FIG. 6, the elongated body may also include a clamp 604 for selectively coupling the mating assembly 600 to the cooling catheter 130. When the clamp 604 is closed, coupling the mating assembly 600 to the cooling catheter 130, a seal is created. In some exemplary embodiments, an additional clamp lock feature (not shown) may be included, such as a snap, a clamp retention clip, or other method of preventing inadvertent release of the clamp 604. When assembled and clamped, any fluid flowing out the proximal end 152 of the drainage catheter 132 can flow out the drainage port 605 of the mating assembly.

Figure 7A:
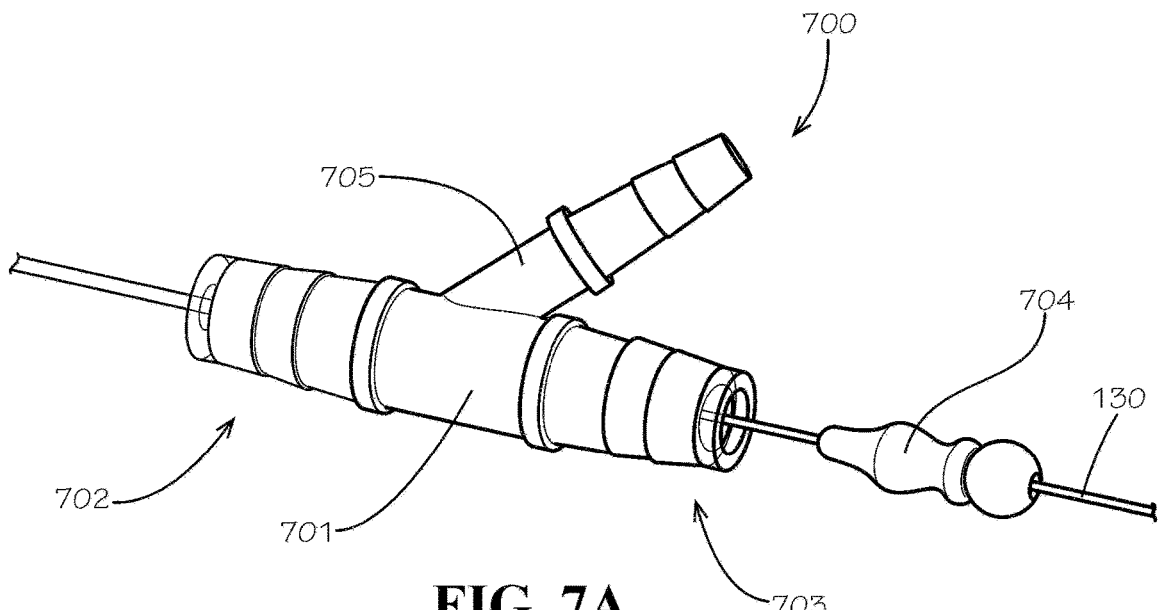
FIG. 7A is a partially-exploded perspective view of another mating assembly in accordance with one example embodiment of the disclosure.
Figure 7B:
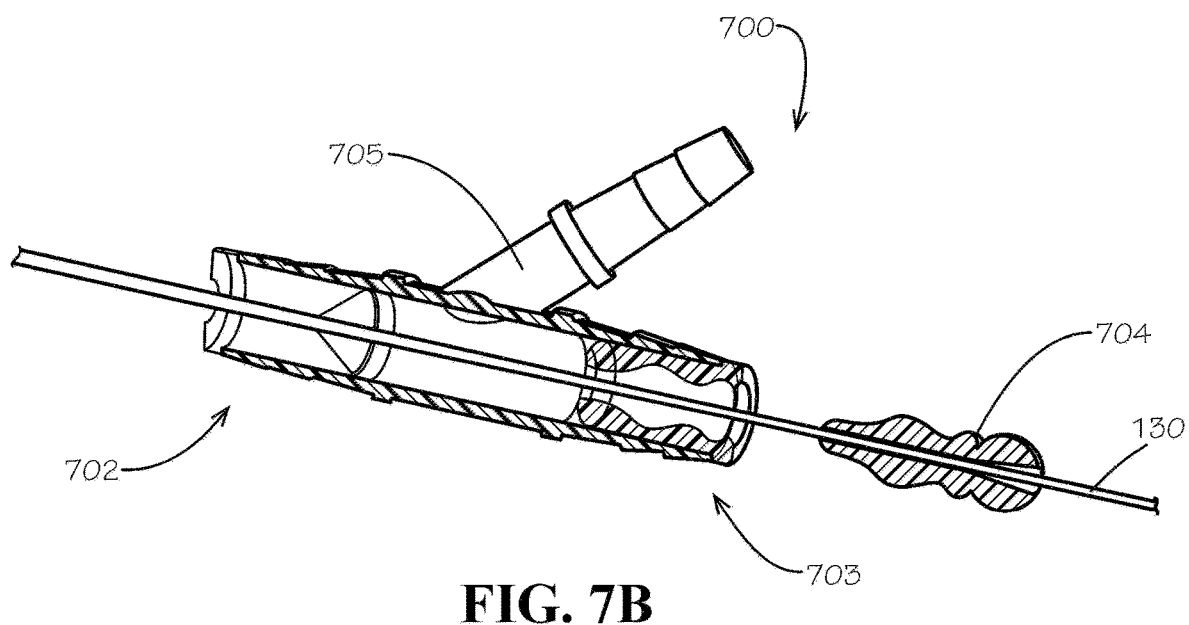
FIG. 7B is sectional view of the mating assembly of FIG. 7A.

In another exemplary embodiment, illustrated in FIGS. 7A and 7B, the mating assembly 700 includes a generally elongated body 701, an attachment end 702, a pass-through end 703, a sealing plug 704, and a drainage port 705 extending outward from a point along elongated body 701. The attachment end 702 is configured to be sealingly attached to the drainage catheter 132, and may be attached using known manufacturing processes like adhesive bonding, overmolding, ultrasonic welding, or other processes known to one of skill in the art. When assembled, the drainage catheter 132 extends partially into the body 701 of the mating assembly 700 as shown in the section view in FIG. 7B. When the drainage catheter 132 is installed coaxially over the cooling catheter 130, the cooling catheter extends through the length of the body 701, extending out the pass-through end 703 of the mating assembly 700. As shown in FIG. 7B, the pass-through end 703 of the mating assembly 700 can be configured to receive the sealing plug 704. The sealing plug 704 is placed over the cooling catheter 130 and slid towards the pass-through end 703 of the mating assembly 700 by the end user. The pass-through end 703 of the mating assembly 700 is configured to receive the sealing plug 704 and compress the sealing plug 704 material when it is fully inserted, creating a seal around the outer surface of the cooling catheter 130. When assembled and the pull plug 704 is fully seated, any fluid flowing out the proximal end 152 of the drainage catheter 132 can flow out the drainage port 705 of the mating assembly.

Figure 8A:
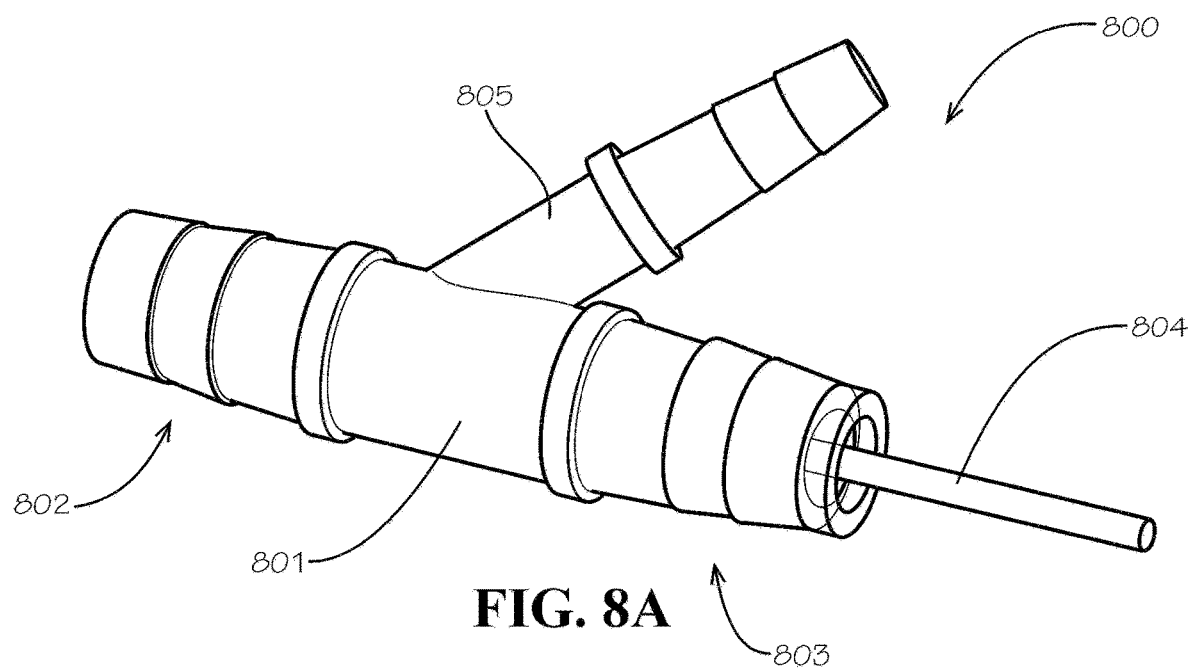
FIG. 8A is a perspective view of another mating assembly in accordance with one example embodiment of the disclosure.
Figure 8B:
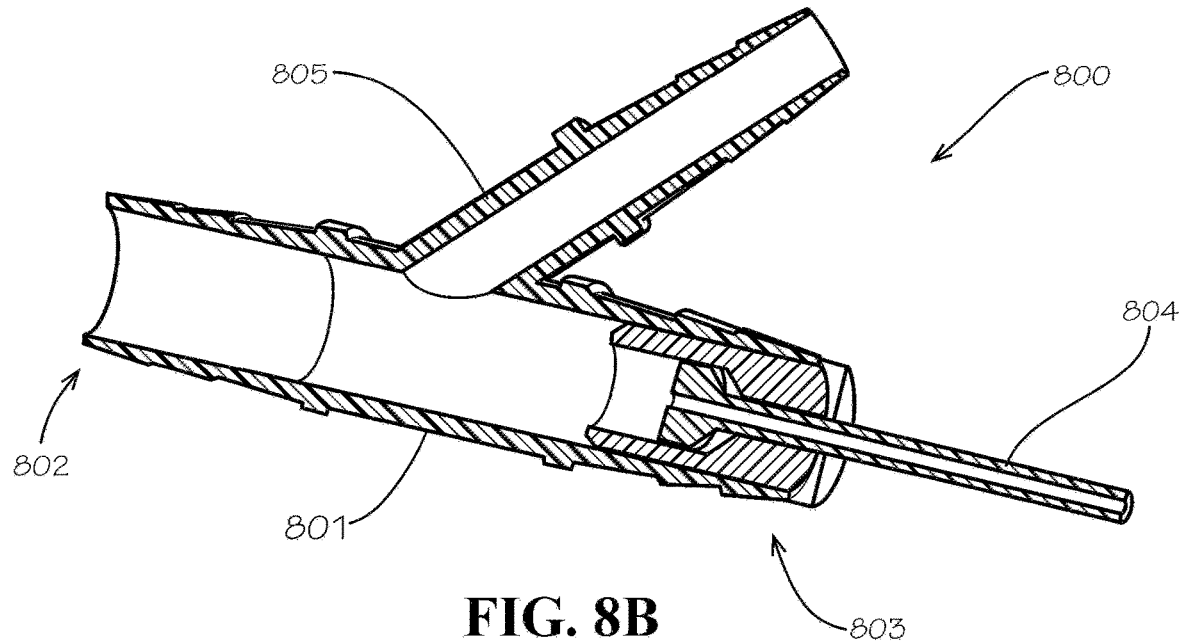
FIG. 8B is a sectional view of the mating assembly of FIG. 8A.

In yet another exemplary embodiment, illustrated in FIGS. 8A and 8B, the mating assembly 800 includes a generally elongated body 801 an attachment end 802, a pass-through end 803, a pull plug 804, and a drainage port 805 extending outward from a point along elongated body 801. The attachment end 802 is configured to be sealingly attached to the drainage catheter 132 (not shown), and may be attached using known manufacturing processes like adhesive bonding, overmolding, ultrasonic welding, or other processes known to one of skill in the art. When assembled, the drainage catheter 132 extends partially into the body 801 of the mating assembly 800. When the drainage catheter 132 is installed coaxially over the cooling catheter 130 (not shown), the cooling catheter extends through the length of the body 801, through a central lumen in the pull plug 804, and extends out the pass-through end 803 of the mating assembly 800. As shown in FIG. 8B, the pass-through end 803 of the mating assembly 800 can be configured to receive the pull plug 804. The pass-through end 803 of the mating assembly 800 is configured to receive the pull plug 804 and compress the pull plug 804 material when the user pulls the pull plug towards the pass-through end 803 until it is fully seated. The pull plug 804 creates a seal around the outer surface of the cooling catheter 130 when fully seated. When assembled and the pull plug 804 is full seated, any fluid flowing out the proximal end 152 of the drainage catheter 132 can flow out the drainage port 805 of the mating assembly.

As explained above, it is desirable to minimize the size of the any dural penetration caused by the catheter assembly 112 because it impacts the ability of the dura to self-heal. When the penetration size is reduced, it may become more difficult or impossible to achieve sufficient cooling to induce the desired localized hypothermia while still allowing for drainage of the CSF. In the example embodiment shown in FIG. 3A, the maximum outside dimension of the catheter assembly is the diameter of the drainage catheter 132. As shown, the drainage catheter has an outer diameter of about 5 Fr, while the cooling catheter placed inside the drainage catheter has an outer diameter of about 4 Fr. As would be understood by one of skill in the art and is discussed in more detail below, other geometries may also be capable of achieving the desired cooling and drainage levels, including round catheter geometries of larger or smaller outer diameters, as well as catheters of varying cross-sectional shapes and areas. Variations on the catheter assembly 112 configuration may be utilized to allow for different cooling, drainage, and self-healing characteristics.

As shown in the section view shown in FIGS. 4B and 4C, the cooling catheter 130 may include two interior lumens or fluid pathways that extend from an opening at the proximal end 163 of the cooling catheter 130 and are in fluid communication with each other towards the distal end 162 of the cooling catheter 130. In these embodiments, the cooling catheter 130 inlet lumen 131 and outlet lumen 133 can be configured to fluidly connect to the first fluid pathway 140 of the tubing set 114 and the second fluid pathway 142 of the tubing set 114, respectively, allowing for the circulation of fluid through the distal end of the cooling catheter.

As shown in FIGS. 3A-3C and discussed above, the drainage catheter 132 may have a generally cylindrical body with a distal end 151, a proximal end 152, an outer surface 153, and a central lumen 134 passing from the distal end 151 to the proximal end 152. Both the distal end 151 and the proximal end 152 of the drainage catheter 132 are open. The proximal end 152 of the drainage catheter 132 is configured to allow for the fluidic connection to a drainage tubing line 144 via the mating assembly (e.g., 500, 600, 700 or 800) discussed above. The distal end 151 of the drainage catheter 132 is open to allow for the flow of CSF into the drainage catheter 132 after placement. As shown in FIG. 4A, the distal end 151 of the drainage catheter 132 may also include a plurality of holes 154 around the outer surface 153 of the drainage catheter 132. These holes 154 create pathways from the outer surface 153 to the central lumen 134 and provide additional pathways for CSF to flow into the drainage catheter 132. The additional holes can both increase the drainage capacity of the catheter, as well as provide additional fluid inlets in the case of partial or total obstruction of one or more of the drainage catheter inlets.

As shown in FIGS. 2 and 3, the drainage catheter 132 is generally shorter than the cooling catheter 130 to allow for exposure of the distal end 162 of the cooling catheter 130 to extend beyond the drainage catheter 132 to increase the possible tissue and fluid contact with the cooled-distal end 162 of the cooling catheter 130. So long as the distal end 151 of the drainage catheter 132 is placed into the intrathecal space, drainage will be possible. Deeper placement of the cooling catheter 130 with respect to the drainage catheter 132 can increase the localized cooling effect by increasing the amount of tissue and fluid in contact with the cooled-distal end 162 of the cooling catheter 130. In embodiments where the cooling catheter 130 and drainage catheter 132 are selectively fixed, the user may adjust not only the insertion depth of the catheter assembly 112 as a whole, but also the insertion depth of the cooling catheter 130 with respect to the drainage catheter 132.

Control of intrathecal pressure is commonly affected by draining small amounts of cerebrospinal fluid to keep pressure within acceptable limits. Although the required drainage rates are very low, the length of CSF drainage catheters and the overall constraints on catheter outer diameter require large drainage lumens to establish the necessary throughput. Existing lumbar drainage catheters have outer diameters greater than 5 Fr and do not contain any additional lumens for recirculation of coolant. With existing drainage catheters (e.g., with outside diameters of 5 Fr or greater), gravity drainage is sufficient to achieve the desired drainage rate. However, cylindrical catheters with an outside dimension of about 5 Fr or smaller, as required to allow the dura to self-seal, will not allow CSF to gravity drain at the desired rate. Accordingly, exemplary embodiments of the cooling and drainage system 100 discussed herein can include a drainage subsystem 200 to improve drainage performance.

Figure 9:
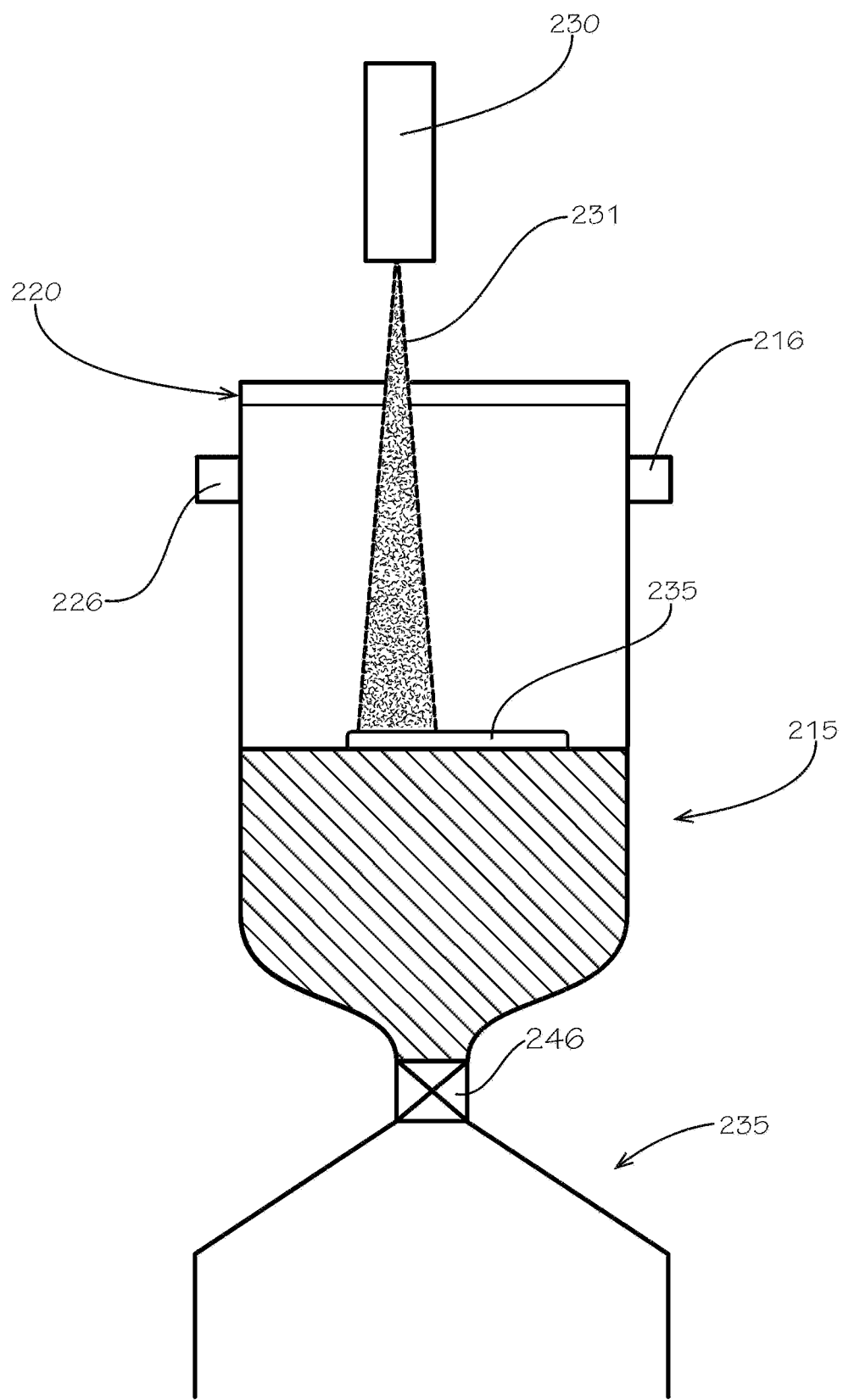
FIG. 9 is a schematic of a drainage collection reservoir and non-contact measuring system in accordance with one example embodiment of the disclosure.
Figure 10:
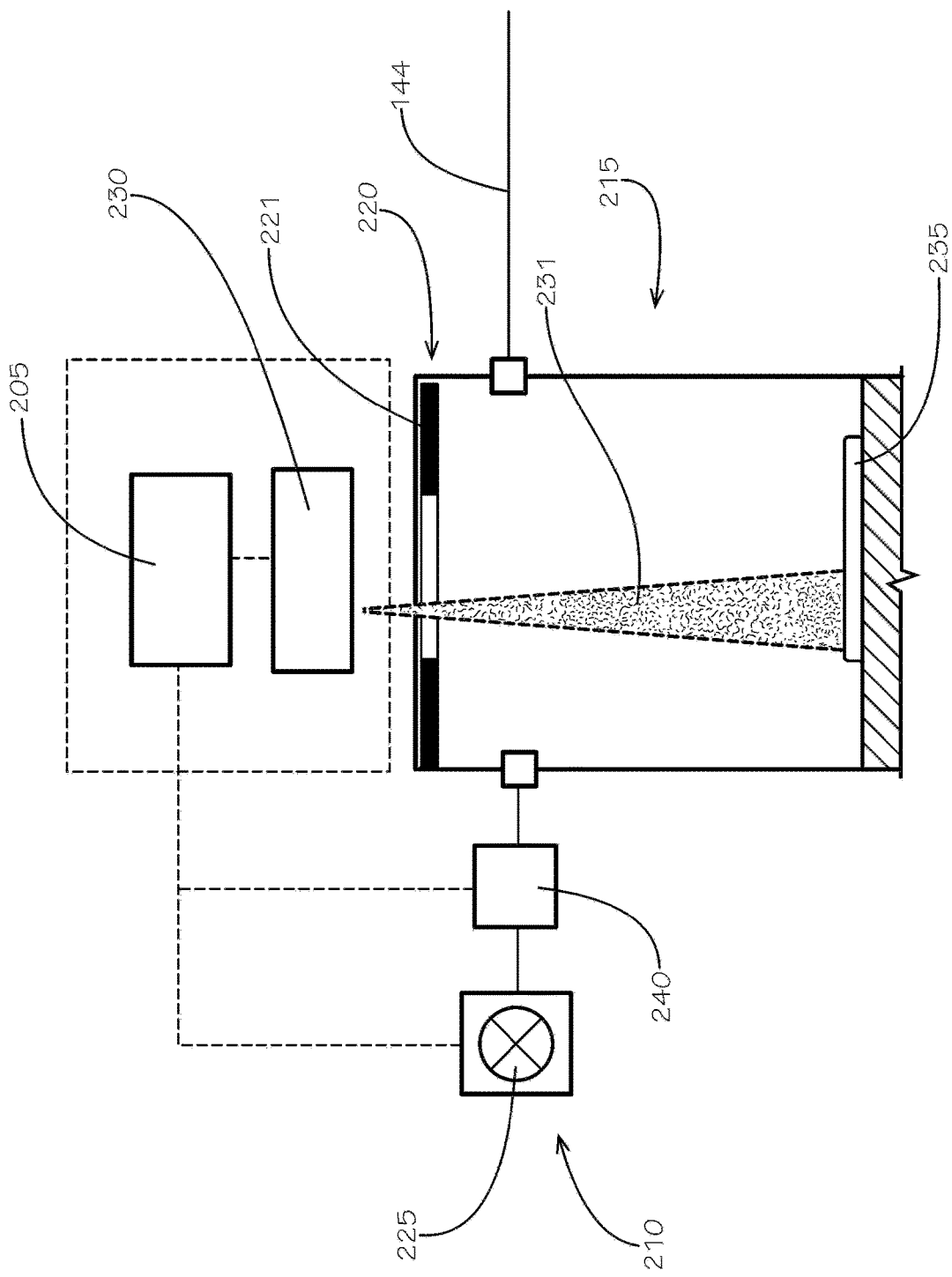
FIG. 10 is a schematic of a non-contact flow rate measuring and drainage control system in accordance with one example embodiment of the disclosure.

As shown in FIG. 1, the drainage subsystem 200 can include a drainage control system 205 and a drainage pump 210 that is operatively connected to the drainage control system 205 and fluidically connected to the drainage tubing line 144 coming from the drainage catheter 132. The drainage subsystem 200 is configured to create or increase the flow of CSF from the drainage catheter 132 through the drainage tubing line 144. Some embodiments contain a collection reservoir 215 that is in fluid communication with the drainage tubing line 144 for collecting the drained CSF. As shown in FIG. 9, The collection reservoir 215 may include a port 216 for connection to the drainage tubing line 144 and a throat orifice 220 that can be used to empty the CSF after use. As illustrated in FIG. 10, some embodiments may also include a removable cap 221 for sealing the collection reservoir 215 by covering the throat orifice 220. In one embodiment, the drainage pump 210 is a syringe pump, for example, the Cole-Parmer EW-74905-19 Four Syringe Pump. Other embodiments may utilize a peristaltic pump or other known type of positive displacement pump, centrifugal pump, diaphragm pump, or rotary pump. Because of the patient-contact nature of CSF drainage, non-contact fluid pumps like peristaltic pumps are desirable to reduce the number of components that must be cleaned, sterilized, or replaced with each use.

The drainage control system 205 can be based on any of the well-known types of industrial controllers, including programmable logic controllers (PLCs), personal computers, single-board computers such as the Raspberry Pi, or a custom-built control solution. In some embodiments, the function of the drainage control system 205 is performed by the control system 120 in the console 110 discussed above, as illustrated in FIG. 1.

The drainage subsystem 200 in some embodiments the drainage pump 210 utilizes a vacuum source 225 to induce the flow of CSF for drainage. As shown in FIG. 1, these embodiments place the collection reservoir 215 between the vacuum source 225 and the drainage catheter 132 (inserted in the intrathecal space). When vacuum is applied to the collection reservoir 215, the vacuum increases the pressure differential between the collection reservoir 215 and the intrathecal space, increasing the CSF flow rate based on the pressure differential as opposed to applying vacuum to suction or siphon CSF from the intrathecal space. In that regard, the system operates on the same principles as a laboratory vacuum trap. In some embodiments, the vacuum source 225 is a vacuum pump. The vacuum pump can be fluidically connected to a vacuum inlet port 226 as shown in FIG. 9 on the collection reservoir 215. Use of the "vacuum trap" drainage system reduces the components subject to replacement by limiting the parts that come in contact with the CSF to the drainage tubing line 144 collection reservoir 215. Other embodiments feature a positive-displacement drainage pump 210, located between collection reservoir 215 and catheter assembly 112. For these embodiments, peristaltic pumps or diaphragm pumps are generally preferred.

As discussed above, intrathecal pressure is typically managed by draining CSF periodically. Measurement of the CSF drainage flow rate in existing gravity drainage systems is relatively crude, relying on the user's visual observation of the volume drained form the patient and collected in a burette over time. Although intrathecal pressure can be monitored directly by inserting pressure monitors into the intrathecal space, it is highly desirable to limit the both the number and size of dural penetrations to reduce the potential for CSF leakage and the need for post procedure intervention. Given the size constraints, it is not possible to insert a pressure sensor into a single 5 Fr dural incision while also accommodating CSF drainage and cooling. Moreover, everything inserted into the intrathecal space should be discarded after each procedure for sterility reasons, so having to dispose of a pressure sensor can increase costs unnecessarily.

The drainage systems disclosed herein include the capability to monitor low CSF flow rates and utilize that CSF flow rate data in the control logic for the drainage control system 205. Alternative inputs including, for example, intrathecal pressure, drainage time, or volume of CSF collected may be used alone or in combination with CSF flow rate data by the drainage control system 205 to control the operation of the drainage subsystem 200. Further, combinations of available flow rate, pressure, time, or volume data may be used by the drainage control system to calculate values like flow rates that may not be directly measured in certain embodiments.

FIGS. 9 and 10 illustrate one exemplary embodiment of the present disclosure that utilizes a non-contact measuring system 230 to monitor CSF drainage and generate CSF drainage data that can be utilized by the drainage control system 205 as described above. In the illustrated embodiment, the non-contact measuring system 230 is an optical measuring system or laser distance sensor, however, the drainage subsystem 200 can utilize any number of non-contact measuring systems including electromagnetic (e.g., laser, microwave, or radio frequency, illustrated as 231) or acoustic energy based systems, as would be apparent to one of skill in the art. As shown, the non-contact measuring system may be configured to take measurements through the open throat orifice 220 or directly through the body of the collection reservoir 215 or the removable cap 221. Alternatively, as would be appreciated by one of skill in the art, the system may utilize other methods to quantify the CSF drainage flow rate such as a contact-based system configured to measure the weight of the CSF drained using a balance, load cell, or other measuring apparatus of sufficient sensitivity.

As shown in FIG. 9, the illustrated embodiment utilizes a laser distance sensor, such as the laser distance measuring units manufactured by di-soric, mounted a fixed distance from the collection reservoir 215. Measurement data generated by the non-contact measuring system 230 is transmitted to the drainage control system 205. Because the collection reservoir 215 has a fixed container volume, distance measurements taken at different time points can be used to calculate the change in volume of fluid in the collection reservoir 215. Utilizing the time between measurements, the flow rate of the fluid in the collection reservoir 215 can be calculated. In some exemplary embodiments, measurements are taken at very short intervals or on a semi-continuous basis to allow for real-time or near real-time monitoring of the CSF flow rate and changes therein. Some exemplary embodiments utilize a float 235, the float 235 is configured to float freely on a volume of fluid collected in the collection reservoir 215 and provide a more consistent point of reference for the non-contact measuring system. The float 235 may be made of a low-density plastic or other buoyant material and is sized to provide a stable orientation within the collection reservoir 215.

As discussed above, data collected by the non-contact measuring system 230 can be transmitted to the drainage control system 205 and used as process control inputs, or, if necessary, used to calculate process control inputs. The drainage control system 205 can use those process control inputs based on the measured or calculated data to modulate the CSF flow rate. In one example embodiment shown in FIG. 10, the drainage control system 205 is operatively connected to the vacuum source and uses the process control inputs to modulate the vacuum pump 225 which, in turn, may increase or decrease the pressure differential between the collection reservoir 215 and the intrathecal space to increase or decrease the CSF drainage flow rate. As shown in FIG. 9, the collection reservoir 215 may optionally be adapted to connect to a drainage reservoir 245. The drainage reservoir 245 may be adapted to selectively attach to the collection reservoir with an intermediate valve or stopcock 246 that can control the flow of fluid between the collection reservoir 215 and the drainage reservoir 245 to increase the capacity of the system in cases involving larger volumes of drained CSF.

In the embodiment shown in FIGS. 1 and 10, the drainage subsystem additionally includes a vacuum regulator 240 to increase control over vacuum levels. As shown in FIGS. 1 and 10, the vacuum regulator can be mounted between the vacuum source 225 and the collection reservoir 215. As shown in FIG. 1, the vacuum system can include a vacuum sensor 247 that may be integrated into the vacuum source 225 or vacuum regulator 240, or otherwise placed between the vacuum source 225 and the collection reservoir 215 to measure vacuum levels. Readings from vacuum sensor 247 can then be used as another input in the drainage control system 205 to control the drainage process, and more specifically, the vacuum source 225.

As referenced above, console 110 includes a cooling system 300 that is configured to control the circulation of coolant between the console 110 and the distal tip 162 of the cooling catheter 130. As illustrated by the example shown in FIG. 1, coolant is pumped through a closed circuit that creates a loop between the cooling catheter 130 and the cooling system components within the console 110. Coolant is chilled and circulated through the distal tip 162 of the cooling catheter 130 to induce localized cooling of tissue and fluid that is in contact with the cooling catheter 130. When coolant leaves the cooling catheter 130 it is routed through a heat exchanger for cooling before returning to the cooling catheter 130. The heat exchanger 301 is a portion of the coolant circuit that is designed to interface with a chiller 122 to allow for the removal of heat from the circulating coolant as the coolant passes through the heat exchanger.

The heat exchanger 301 may be any of several types of heat exchangers that can be configured to chill the circulating coolant to a level sufficient to induce localized hypothermia in the patient, generally until the CSF reaches a target of about 24 to 32 degrees Celsius. The heat exchanger 301 may cool the coolant in combination with a chiller utilizing any one of a number of known cooling technologies, including the use of vapor-compression refrigeration, thermoelectric cooling, or by submerging the heat exchanger 301 in a chilled bath or cooler in a liquid-liquid or liquid-air cooling configuration.

The chiller 122 may be any type of refrigeration unit capable of removing heat from the heat exchanger 301 at a rate sufficient to achieve the desired CSF temperature. Coolant is chilled by placing the heat exchanger 301 in sufficient proximity to the chiller 122 to allow heat to transfer conductively from the coolant, through the heat exchanger 301, to the chiller 122. Uniform contact between the heat exchanger 301 and the chiller 122 provides optimum cooling through conduction, however, based on the configuration of the heat exchanger 301, irregularities or gaps between the heat exchanger 301 and the chiller 122 may reduce cooling effectiveness or result in less efficient convective heat transfer between the chiller and the heat exchanger 301.

Figure 11:
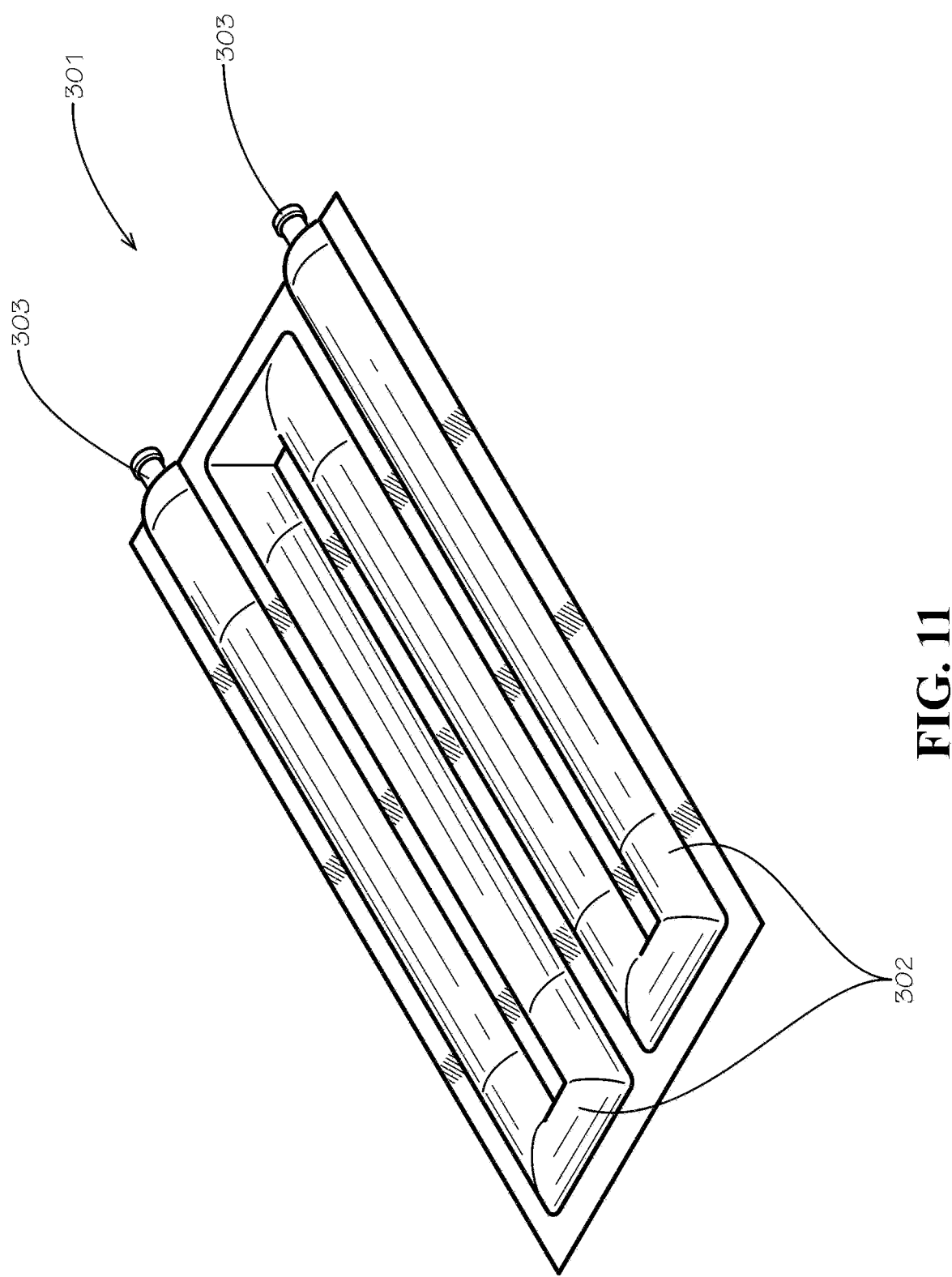
FIG. 11 is a perspective drawing of a "pouch"-type heat exchanger in accordance with one example embodiment of the disclosure.
Figure 12:
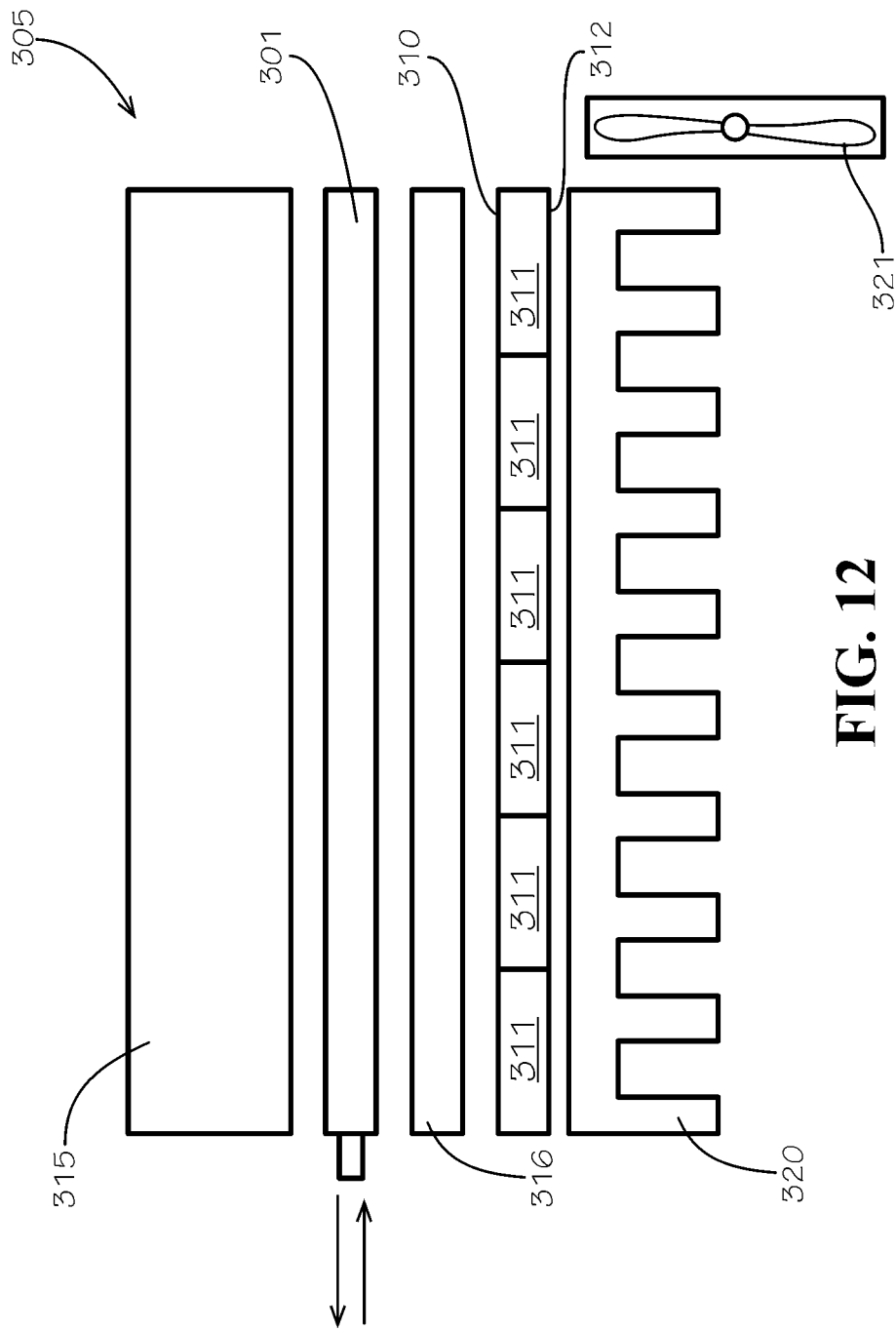
FIG. 12 is an exploded schematic of a thermoelectric chiller subsystem in accordance with one example embodiment of the disclosure.
Figure 13:
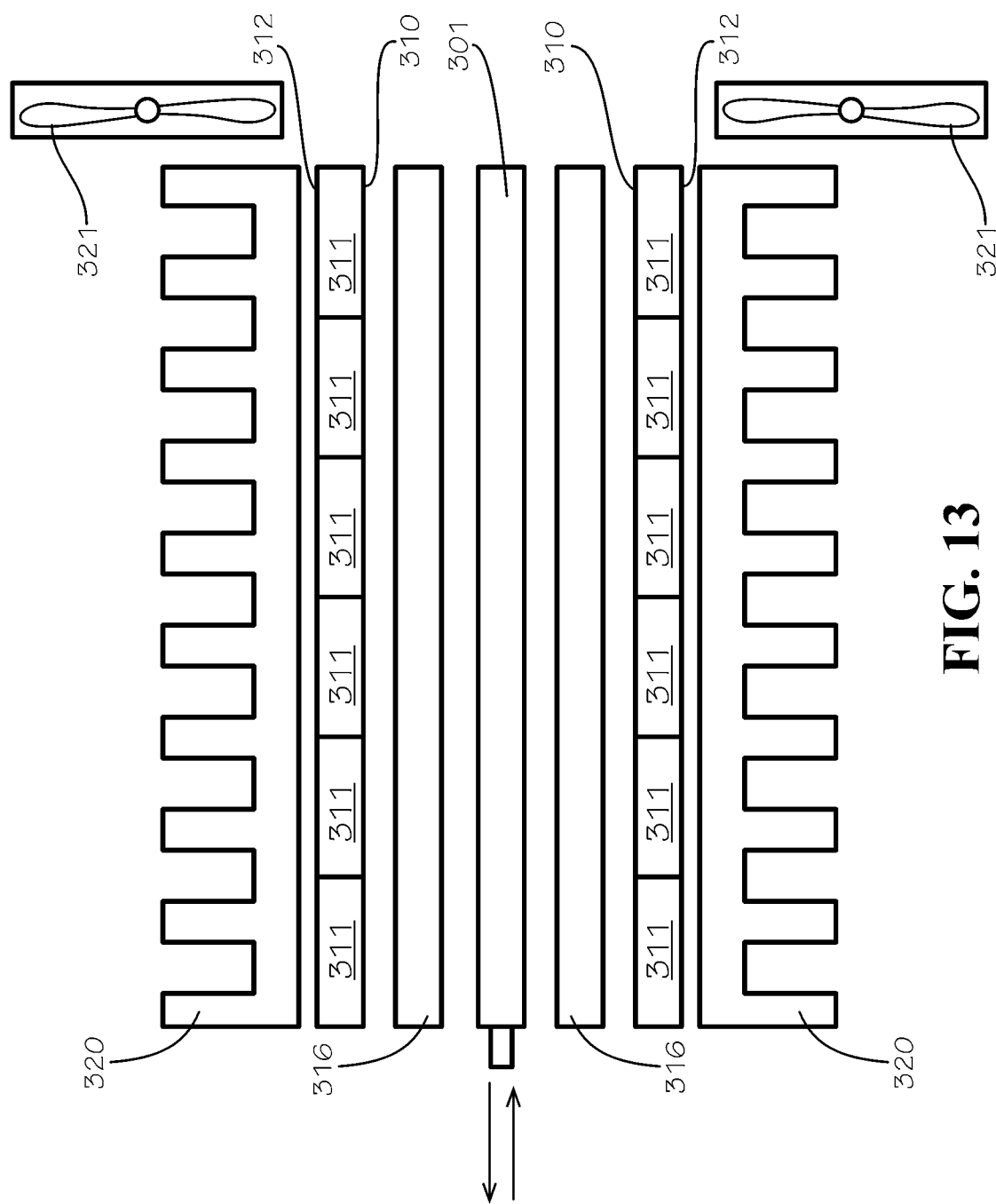
FIG. 13 is a partially exploded schematic of another thermoelectric chiller subsystem in accordance with one example embodiment of the disclosure.
Figure 15:
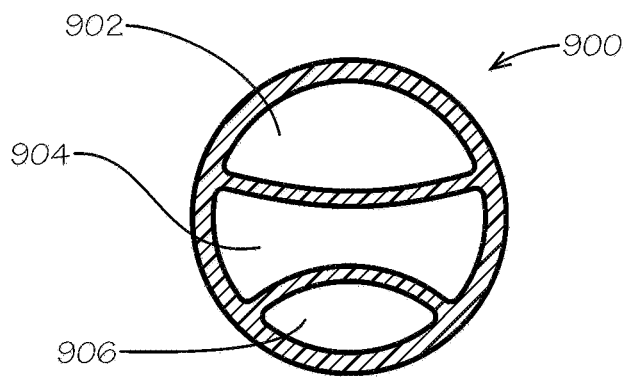
FIG. 15 is a cross-sectional view of a multi-lumen drainage and cooling catheter assembly in accordance with one example embodiment of the disclosure.
Figure 16:
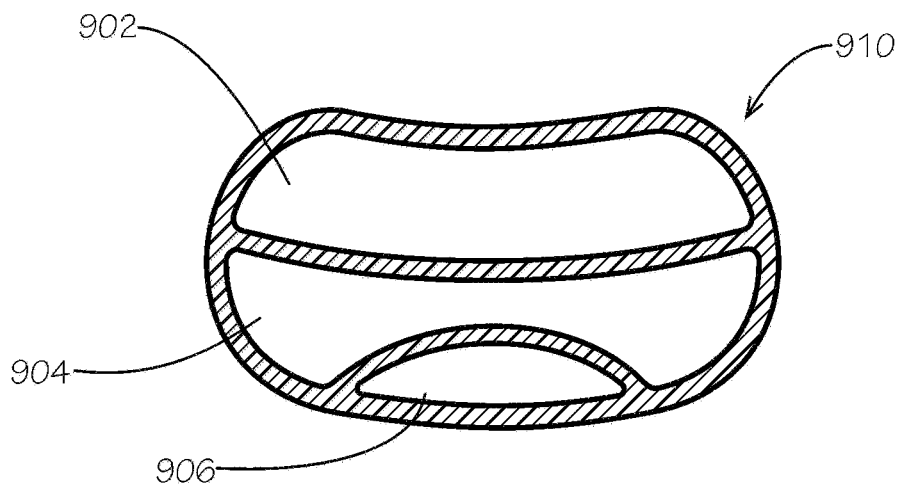
FIG. 16 is a cross-sectional view of another multi-lumen drainage and cooling catheter assembly in accordance with one example embodiment of the disclosure.

In one example embodiment, shown in FIGS. 11-13, the chiller 122 that the heat exchanger 301 is paired with is a thermoelectric cooler 305, sometimes referred to as a Peltier device, a Peltier cooler, a Peltier heat pump, or a solid-state refrigerator. Thermoelectric coolers operate on the Peltier effect where DC current is run through a cooling element, transferring heat from one side of the cooling element to the other, resulting in a "hot side" and a "cool side" of the cooling element. Traditionally, the hot side of the cooling element is attached to a heat sink so that it remains at ambient temperature, causing the cool side temperature to fall below room temperature. By cascading multiple cooling elements together, the cooling effect can be increased.

FIG. 12 shows an exploded view of one embodiment of the present disclosure incorporating a thermoelectric cooler 305. As shown, the heat exchanger 301, which includes a fluid-pathway for the coolant to circulate through, is removably placed into the thermoelectric cooler 305, adjacent to the "cool side" 310 of the individually-replaceable thermoelectric modules 311.

In some embodiments, the chiller is configured to selectively secure the heat exchanger within the chiller; this may occur, by utilizing a weighted plate 315 to secure the heat exchanger 301 in place (as illustrated in FIG. 12), or by utilizing a clamping or locking mechanism to secure the heat exchanger 301 and optionally, apply clamping pressure to part of or across all of the heat exchanger 301 to promote uniform contact with thermoelectric modules 311 via conduction plate 316 which is made of metal or other heat-conductive material. A heat sink 320, attached to the hot side 312 of the thermoelectric modules 311, is cooled with a fan 321 that circulates air past the heat sink 320.

FIG. 13 illustrates another exemplary embodiment of a chiller 122 utilizing two thermoelectric coolers. In this embodiment, instead of using a weighted plate 315 to press the heat exchanger 301 against the conduction plate 316, the heat exchanger is sandwiched between two coolers, each with sets of thermoelectric modules 311, conduction plates 316, heat sinks 320, and cooling fans 321. The two chiller assemblies may be utilized, for example, with a rigid heat exchanger that can be removably inserted between the two chillers, or one or more of the chillers may be repositionable to allow for the insertion of the heat exchanger. Thermoelectric modules 311 typically consist of alternating p- and n-type semiconductors sandwiched between ceramic plates. As explained above, when a direct current is applied to the modules, heat flows through the plates and semiconductors due to the Peltier effect. When in use, heat is transferred from the coolant in the heat exchanger 301 through conduction plate 316 through the thermoelectric modules 311 to the heat sinks 320, which radiate this heat to the surrounding air circulated using cooling fans 321. Although less efficient than heat exchangers using a liquid refrigerant (i.e. vapor compression refrigeration), thermoelectric cooling is mechanically simpler, more compact, and avoids the presence of potentially-hazardous refrigerants in the operating room.

Although the heat exchanger 301 can be made from a wide variety of materials in a wide number of configurations, utilizing a flexible or conformable "pouch" configuration as shown in FIG. 11 provides many benefits. First, as referenced above, gaps between the heat exchanger and the thermoelectric cooler can have significant negative impact on the systems cooling capability, even minor variations along the length of the heat exchanger may drastically reduce cooling capability. As such, rigid heat exchangers require very high manufacturing tolerances to achieve peak performance and removable heat exchangers, which may be desired as discussed below, may lead to additional variability from the replacement process. By utilizing a heat exchanger that is flexible, semi-rigid, or otherwise capable of conforming to the chiller, contact between the heat exchanger and the chiller can be improved and variability reduced.

Flexible heat exchangers include many other benefits, including lower costs, easier installation, and increased flexibility for sizing and fluid pathways. As shown in FIG. 11, the heat exchanger may incorporate a multiple-pass coolant pathway 302 that increases the area in contact with the chiller and increases the time the coolant is exposed to the chiller by lengthening the pathway. In one example embodiment, the flexible heat exchanger is made from two pieces of aluminum foil laminate film that are heat sealed together to create the fluid pathway 302, although any number of other flexible, heat conductive materials may be used. The flexible heat exchanger may incorporate adapters 303 that allow for the removable connection to tubing, or tubing may be fixed to the flexible heat exchanger by heat sealing, adhesive bonding, ultrasonic welding, or other techniques. Because the coolant circulates through the cooling catheter within the patient's body, it is desirable to replace any system components that come in direct contact with the coolant, prior to each use of the system.

The embodiments disclosed herein, and specifically the single-use disposable components including the catheters, tubing sets, and heat exchangers, may be provided in a kit containing some or all of the additional components used during their operative use by end users. In some embodiments of the present disclosure, the kits may include an access kit. The access kit includes components that are designed to facilitate insertion of the catheter assembly 112 into the intrathecal space as described above. In one such embodiment, the kit may include an introducer needle, such as a 14-gauge Tuohy needle assembly. During placement, the user would first insert the needle through the patient's skin until it entered the desired intrathecal space. Once placed, the catheter assembly 112 is passed through a central lumen of the introducer needle. In some exemplary embodiments, the introducer needle also includes a peelable sheath mounted outside of the introducer needle. After the needle is placed, the needle can be retracted leaving the peelable sheath in place which provides a pathway to insert the catheter assembly 112. Once the catheter assembly has been inserted, the peelable sheath may be peeled away, leaving the catheter assembly 112 in place.

In some embodiments of the present disclosure, kits are provided in one or more pre-packaged sterile trays, for example, a thermoformed PTFE tray configured to securely hold the components during use with a heat-sealed Tyvek lid. Other packaging configurations may of course be provided, including packaging components in pouches, plastic or paper backings, or protective outer corrugate shipping containers.

As referenced above, the catheter assembly 112 may come in a wide variety of configurations, including catheters that use geometries that are not round or cylindrical. As shown in FIGS. 3B and 3C, catheter assemblies may include more than one outer diameter.

In one exemplary embodiment, shown in FIG. 14A, the cross-section of a cooling catheter assembly 130 varies over its length, and the profile changes from round at its proximal end 1401, to oblong or crescent-shaped cross section at its distal end 1402, with two interior lumens as shown in the cross-sectional view shown in FIG. 14B. The proximal end 1401 has a round overall cross section with an outer diameter of about 5 Fr. The distal end 1402 shown has a thickness of about 5 Fr, but a width of about 11 Fr. During insertion, the larger cross-sectional areas are compressed, allowing them to fit into a smaller introducer needle or insertion hole. As shown, the catheter is configured to compress into a 5 Fr maximum diameter for insertion. Once inserted, the natural resilience of the flexible material causes expansion to the originally-extruded 11 Fr width. Examples embodiments of these catheters may be made from, for example, extruded polyurethane or Pebax, and complex geometries may be extruded or made from more than one piece and joined with adhesives, RF, thermal, or ultrasonic welding, or other commonly known joining process.

Similarly, in addition to multi-piece assemblies with separate cooling catheter 130 and drainage catheter 132 assemblies, the catheter assembly 112 may be provided in a single-catheter configuration with three or more lumens as discussed below. Exemplary multi-lumen embodiments, like those shown in FIGS. 15-17, may include at least a coolant inlet lumen 902, a coolant outlet lumen 904, and a drainage lumen 906. In some exemplary embodiments, one or more of the lumens may be collapsible, meaning, when fluid flows through at least a portion of the catheter, the walls of one or more of the lumens may compress or expand.

Figure 18:
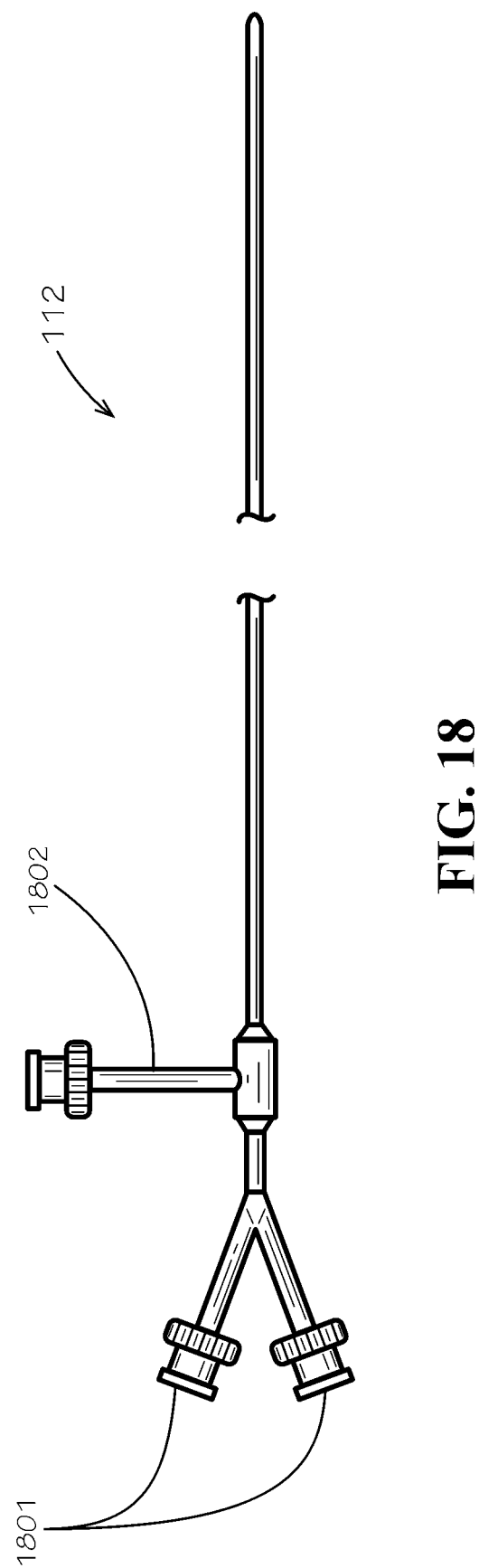
FIG. 18 is a schematic of a multi-lumen drainage and cooling catheter assembly in accordance with one example embodiment of the disclosure.

Multi lumen catheters may include several configurations. Because the coolant inlet lumen 902 and coolant outlet lumen 904 need to be in fluid communication with each other at the distal end of the catheter, they may be adjacent to each other, so as not to interfere with the drainage lumen 906, or, alternatively, the drainage lumen may only run a portion of the length of the catheter, allowing the inlet and outlet lumens to connect proximally to the stoppage of the drainage lumen. In some example embodiments, the catheters include a collapsible drainage lumen 906 adjacent to the coolant inlet lumen 902 and coolant outlet lumen 904 that merge at or near the tip of the catheter. The catheter 910 shown in FIG. 16 conforms to the shape of the spinal cord, and its overall shape provides greater surface area, both factors enhancing heat transfer. Although the drainage lumen 906 could extend for the entire length to the distal end, this reduces the cross-sectional area available for coolant flow and heat exchange. Therefore, certain embodiments of the catheter utilize varying cross sections (as illustrated in FIG. 14A) and varying lumens along their lengths. FIG. 18 shows an exemplary embodiment of a single-lumen catheter assembly 112, complete with y-attachments 1801 for connecting the coolant inlet and outlet lumens to the tubing set 114, and a drainage port 1802 for connecting the drainage lumen to the collection reservoir.

Figure 17:
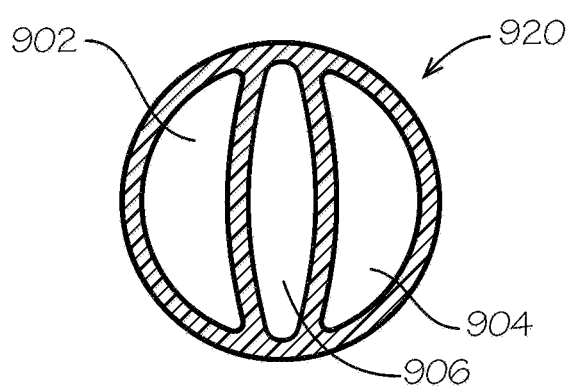
FIG. 17 is another cross-sectional view of a multi-lumen drainage and cooling catheter assembly in accordance with one example embodiment of the disclosure.

The embodiment of catheter 920 shown in FIG. 17 may be used with alternating cooling and drainage (ACAD) cycles. ACAD takes advantage of the fact that, due to the thermodynamic characteristics of CSF (which is primarily water), it is not necessary to continuously cool it in order to keep it within the desired temperature for localized hypothermia. This embodiment effectively allows "timesharing" of the limited cross-sectional area of the catheter. In this embodiment, coolant pump 124, operates to circulate coolant through lumens 902 and 904 through coolant lines 140 and 142. Lumens 902 and 904 are in fluid communication at the distal end of the catheter. This catheter features a collapsible third lumen 906 for CSF drainage. During operation of the coolant pump 124, when coolant is flowing through lumens 902 and 904, the coolant fluid pressure causes lumen 906 to collapse. Coolant is allowed to circulate until the CSF reaches the desired temperature (e.g., 24-32 degrees Celsius). At this point, the coolant pump 124 is turned off. Without coolant flowing, the natural resiliency of the catheter and the CSF pressure causes lumen 906 to return to an open position and permit CSF to drain. Drainage pump 210 is turned on to promote flow of CSF and permitting CSF to drain into the collection reservoir 215.

As an illustrative example of ACAD, assume 20 mL of CSF must be removed from the intrathecal space every hour. Coolant pump 124 is activated causing coolant to flow until the desired temperature is reached. Every 15 minutes, active cooling will cease, i.e. coolant pump 124 is shut off and drainage pump 210 is activated. CSF drainage will commence for 2 minutes, draining 5 mL (2.5 mL/min) of CSF. Following the drainage period, cooling will resume. This cycle is repeated until drainage or cooling is no longer needed. Since continuous cooling is not necessary to keep the CSF within the desired temperature range, the serial draining, and cooling method described above optimizes the catheter geometry within the given size constraints.

In one example embodiment of the present disclosure, a spinal cooling and drainage apparatus includes a drainage and cooling catheter assembly that is adapted for intrathecal insertion into a patient. The catheter assembly is adapted for intrathecal insertion into a patient, that is, insertion into the intrathecal space of a patient. The catheter assembly includes an insertion portion and a working end portion, the insertion portion being the portion configured for inserted into the patient, while the working end portion being the working end of the catheter assembly that remains outside of the patient's body. In one example embodiment, the maximum cross-sectional dimension of the insertion portion of the drainage and cooling catheter assembly may be between about 7 Fr and about 5 Fr. In some exemplary embodiments the maximum cross-sectional dimension of the insertion portion of the drainage and cooling catheter assembly may be about 5 Fr. In some exemplary embodiments the maximum cross-sectional dimension of the insertion portion of the drainage and cooling catheter assembly may be about 4 Fr. The spinal cooling and drainage apparatus also includes a console.

In one example embodiment, the console includes a drainage pump and a drainage control system. The drainage control system can be operatively connected to the drainage pump and be configured to control the rate of drainage of cerebrospinal fluid from a patient. The console can also include a cerebrospinal fluid collection reservoir that can be fluidly coupled to the drainage and cooling catheter assembly. A float may be included that is sized to float freely on a volume of cerebrospinal fluid collected in the collection reservoir. The console may also include a coolant pump that is coupled to the drainage and cooling catheter assembly and is configured to circulate coolant between the drainage and cooling catheter assembly and the console. The console may also include a chiller assembly, that can include a thermoelectric cooling unit.

In some example embodiments the drainage control system includes a non-contact measuring system adapted (a) to measure a first distance to the float at a first time point and generate a first signal corresponding to the first distance and the first time point; and (b) measure a second distance to the float at a second time point and generate a second signal corresponding to the second distance and the second time point. The drainage control system may also include a controller that is adapted to (a) calculate a flow rate based on at least the first signal and the second signal, and (b) generate a drainage pump control signal based on the calculated flow rate.

In one example embodiment the drainage pump in the console is a vacuum pump and the console also includes a vacuum regulator. The vacuum pump and the vacuum regulator may be operatively connected to the drainage control system controller so that the drainage control system controller may control the operation of the vacuum pump and the vacuum regulator. In some embodiments, the vacuum pump is fluidly connected to the collection reservoir and the vacuum regulator is mounted between the vacuum pump and the collection reservoir. In these embodiments, the vacuum regulator can be configured to modulate the vacuum level applied to the collection reservoir based on the drainage pump control signal, modulating the drainage flow rate.

In one example embodiment, the catheter assembly includes a drainage catheter, a drainage tubing set, a cooling tubing set, and a cooling catheter. The drainage catheter may have a cylindrical body with a proximal end, an open distal end, and a central lumen passing between the proximal and distal ends. The drainage tubing set can be adapted to fluidly couple the proximal end of the drainage catheter to the collection reservoir. The cooling tubing set may include a coolant inlet line and a coolant outlet line. The cooling catheter may have a proximal end and closed distal end where the proximal end is adapted to couple (a) the coolant inlet line to a first interior lumen of the cooling catheter and (b) the coolant outlet line to a second interior lumen of the cooling catheter. In some embodiments, the first interior lumen and the second interior lumen of the cooling catheter are in fluid communication near the closed distal end of the cooling catheter. Finally, the coolant inlet line and the coolant outlet line may be configured to fluidly couple the cooling catheter to the chiller assembly and allow for closed-loop circulation of coolant between the console and catheter assembly.

In some exemplary embodiments, the drainage catheter may also include a plurality of holes that pass from the outer surface of the drainage catheter to the open central lumen. In some embodiments these holes may be located toward the distal end of the drainage catheter. In some embodiments, the cooling catheter is configured to be passed through the central lumen of the drainage catheter and sized so that there remains a gap that can allow cerebrospinal fluid to flow between the inner wall of the central lumen of the drainage catheter and an outer wall of the cooling catheter. In some embodiments, the cooling catheter assembly is comprised of polyurethane that is reinforced with an embedded mesh structure.

In other exemplary embodiments, the drainage and cooling catheter assembly is a multi-lumen catheter that includes a drainage lumen, a coolant inlet lumen, and a coolant outlet lumen. The distal end of the drainage lumen can be adapted to be in fluid communication with an intrathecal cavity of a patient when the catheter assembly is inserted, and the inlet lumen and outlet lumen can be in fluid communication with each other at the distal end of the multi-lumen catheter to allow for looped circulation of coolant through the multi-lumen catheter.

In another embodiment of the present disclosure, a spinal cooling and drainage system includes a catheter system with a cooling catheter, a tubing set, and a console. The console may include a fluid cooling system with coolant and a thermoelectric cooling unit, a circulation system, and a control system. The tubing set may be configured to connect the cooling system to the catheter system and allow the closed-loop circulation of the coolant between the cooling system and the cooling catheter. The circulation system can be configured to control the flow of the coolant between the cooling system and the catheter system as it circulates through the closed loop.

In some example embodiments the cooling catheter may have a proximal end and a distal end and be configured to allow circulation of the coolant through an inlet lumen and an outlet lumen within the cooling catheter, the inlet lumen and outlet lumen being fluidly connected to each other near the distal end of the cooling catheter and each fluidly connected to the tubing set at the proximal end of the cooling catheter. In one example embodiment, the maximum cross-sectional dimension of a distal portion of the catheter assembly, that is, the portion inserted into the patient, may be between about 7 Fr and about 5 Fr. In some exemplary embodiments the maximum cross-sectional dimension of a distal portion of the catheter assembly may be about 5 Fr. In some exemplary embodiments the maximum cross-sectional dimension of a distal portion of the catheter assembly may be about 4 Fr.

In some examples, the spinal cooling system also includes drainage system. The drainage system can include a drainage catheter, a drainage tubing set, a collection reservoir, and a drainage control apparatus. The drainage tubing set can fluidly connect the drainage catheter to the collection reservoir. The drainage catheter can be configured to allow for the removable insertion of the cooling catheter, where the cooling catheter can be removably coaxially inserted through a central lumen of the drainage catheter. The drainage catheter may include a proximal end and a distal end where the distal end of the drainage catheter is configured for insertion into a patient and the proximal end of the drainage catheter is configured for connection to the drainage tubing set.

In some example embodiments, the drainage control apparatus includes a vacuum source fluidly connected to the collection reservoir and a feedback system operatively connected to the control system that is configured to control the vacuum source. In some embodiments, the feedback system includes a non-contact measuring system and a float that is adapted to float on a volume of fluid collected in the collection reservoir. The feedback system may be configured to generate feedback data based on readings from the non-contact measuring system. The drainage control system may also be configured to control the vacuum source based on the feedback data to modulate CSF flow rates through the drainage catheter.

In some embodiments, the console also includes a coolant circuit with an integrated heat exchanger. The coolant circuit can be configured to fluidly connect the fluid cooling system, the tubing set, and the catheter system, allowing coolant to be circulated in a closed-loop by the circulation system. The heat exchanger may be adapted to interface with the thermoelectric cooling unit to remove heat from the circulating coolant. In some embodiments, the heat exchanger is a flexible pouch configured to be selectively inserted into the thermoelectric cooling system.

All of the embodiments set forth herein are illustrative only of the inventive concept represented by the claims and should not be construed to limit the scope of the invention as set forth in the claims. Other aspects, advantages, modifications, and combinations will be apparent to those skilled in the art to which the invention pertains, and these aspects and modifications are within the scope of the invention, which is limited only by the appended claims. Although examples of specific components and configurations have been presented in the embodiments herein, the invention is not limited to such materials or dimensions unless specifically required by the language of a claim. The components and configurations presented in the embodiments herein can be rearranged and combined in manners other than as specifically described above, with any and all alternative permutations and combinations remaining within the scope of the invention as defined by the claims.

What is claimed is:

1. A spinal cooling and drainage apparatus, comprising:
   a drainage and cooling catheter assembly adapted for intrathecal insertion into a patient, the drainage and cooling catheter assembly comprising:
      a working end portion;
      an insertion portion having a maximum cross-sectional dimension of about 5 Fr;
      a drainage catheter having a proximal end, a distal end open to cerebrospinal fluid flow, and a central lumen passing therebetween; and
      a cooling catheter having a proximal end, a closed distal end, a first interior lumen, and a second interior lumen in fluid communication with the first interior lumen near the closed distal end of the cooling catheter, the cooling catheter configured to be passed through the central lumen of the drainage catheter such that there is a gap permitting cerebrospinal fluid flow between an inner wall of the central lumen of the drainage catheter and an outer wall of the cooling catheter; and
   a console, comprising:
      a drainage pump;
      a cerebrospinal fluid collection reservoir fluidically coupled to the drainage and cooling catheter assembly and configured to collect cerebrospinal fluid;
      a drainage control system operatively connected to the drainage pump and configured to control a rate of drainage of cerebrospinal fluid from a patient, wherein the drainage control system comprises a non-contact measuring system configured to monitor a volume of cerebrospinal fluid collected inside the cerebrospinal fluid collection reservoir;
      a coolant pump coupled to the drainage and cooling catheter assembly and configured to circulate a coolant between the drainage and cooling catheter assembly and the console; and a chiller assembly comprising a thermoelectric cooling unit;

wherein the drainage catheter is adapted to be fluidically coupled to the cerebrospinal fluid collection reservoir; and wherein the cooling catheter is adapted to be fluidically coupled to the chiller assembly for accepting and returning the coolant thereto.

2. The apparatus of claim 1, wherein:

the cerebrospinal fluid collection reservoir comprises a float sized to float freely on a volume of cerebrospinal fluid collected inside the cerebrospinal fluid collection reservoir;

the non-contact measuring system is adapted to (a) measure a first distance to the float at a first time point and generate a first signal corresponding to the first distance and the first time point, and (b) measure a second distance to the float at a second time point and generate a second signal corresponding to the second distance and the second time point; and the drainage control system further comprises a controller adapted to (a) calculate a flow rate based on at least the first signal and the second signal, and (b) generate a drainage pump control signal based on the calculated flow rate.

3. The apparatus of claim 2, wherein the console further comprises a vacuum regulator, and wherein the drainage pump is a vacuum pump, the vacuum pump and the vacuum regulator being operatively connected to the controller of the drainage control system.

4. The apparatus of claim 3, wherein the vacuum pump is fluidically connected to the cerebrospinal fluid collection reservoir, wherein the vacuum regulator is mounted between the vacuum pump and the cerebrospinal fluid collection reservoir, and wherein the vacuum regulator modulates a vacuum level applied to the cerebrospinal fluid collection reservoir based on the drainage pump control signal.

5. The apparatus of claim 1, wherein the drainage and cooling catheter assembly further comprises:

a drainage tubing set adapted to fluidically couple the proximal end of the drainage catheter to the cerebrospinal fluid collection reservoir; and a cooling tubing set comprising a coolant inlet line and a coolant outlet line;

wherein the proximal end of the cooling catheter is adapted to couple (a) the coolant inlet line to the first interior lumen of the cooling catheter and (b) the coolant outlet line to the second interior lumen of the cooling catheter; and wherein the coolant inlet line and the coolant outlet line fluidically couple the cooling catheter to the chiller assembly.

6. The apparatus of claim 5, wherein the drainage catheter further comprises a plurality of holes passing from an outer surface of the cylindrical body to the central lumen, the plurality of holes being located towards the distal end of the drainage catheter.

7. The apparatus of claim 1, wherein the drainage and cooling catheter assembly is comprised of polyurethane with a reinforcing mesh structure embedded therein.

8. The apparatus of claim 1, wherein the drainage and cooling catheter assembly comprises: a multi-lumen catheter comprising a drainage lumen, a coolant inlet lumen, and a coolant outlet lumen, wherein a distal end of the drainage lumen is adapted to be in fluid communication with an intrathecal cavity of a patient, and wherein the coolant inlet lumen and the coolant outlet lumen are in fluid communication with each other at a distal end of the multi-lumen catheter.

9. A spinal cooling and drainage system comprising:

a catheter assembly comprising a cooling catheter and a drainage catheter, wherein the cooling catheter is configured to be removably inserted through a central lumen of the drainage catheter;

a tubing set; and a console comprising:

a cooling system comprising a thermoelectric cooling unit and a coolant;

a circulation system; and a control system;

wherein the tubing set fluidically connects the cooling system to the catheter assembly and is configured to allow circulation of the coolant between the cooling system and the cooling catheter; and wherein the circulation system is configured to control a flow of the coolant between the cooling system and the catheter assembly.

10. The spinal cooling and drainage system of claim 9, wherein the cooling catheter has a proximal end and a distal end and is configured to allow circulation of the coolant though an inlet lumen and an outlet lumen within the cooling catheter, the inlet lumen and the outlet lumen being fluidically connected to each other near the distal end of the cooling catheter and each fluidically connected to the tubing set at the proximal end of the cooling catheter.

11. The spinal cooling and drainage system of claim 9, wherein a distal portion of the catheter assembly is configured for insertion into a patient and has a maximum outside dimension of about 5 Fr.

12. The spinal cooling and drainage system of claim 9, wherein a distal portion of the catheter assembly is configured for insertion into a patient and has a maximum outside dimension of about 4 Fr.

13. The spinal cooling and drainage system of claim 9, further comprising a drainage system comprising a drainage tubing set, a collection reservoir, and a drainage control apparatus, the drainage tubing set fluidically connecting the drainage catheter to the collection reservoir.

14. The spinal cooling and drainage system of claim 13, wherein the drainage catheter comprises a proximal end and a distal end, the distal end of the drainage catheter being configured for insertion into a patient, the proximal end of the drainage catheter being configured for connection to the drainage tubing set.

15. The spinal cooling and drainage system of claim 13, wherein the drainage control apparatus comprises a vacuum source fluidically connected to the collection reservoir and a feedback system operatively connected to the control system.

16. The spinal cooling and drainage system of claim 15, wherein the feedback system comprises a non-contact measuring system and a float configured to float on a volume of fluid collected in the collection reservoir, and wherein the feedback system is configured to generate feedback data based on readings from the non-contact measuring system.

17. The spinal cooling and drainage system of claim 16, wherein the drainage control apparatus is configured to control the vacuum source based on the feedback data to modulate a flow rate of cerebrospinal fluid through the drainage catheter.

18. The spinal cooling and drainage system of claim 9, wherein the console further comprises a coolant circuit comprising a heat exchanger, the coolant circuit fluidically connecting the cooling system, the tubing set, and the catheter assembly, allowing the coolant to be circulated in a closed-loop by the circulation system, and wherein the heat exchanger is adapted to interface with the thermoelectric cooling unit to remove heat from the circulating coolant.

19. The spinal cooling and drainage system of claim 18, wherein the heat exchanger comprises a flexible pouch configured to be removably inserted into the thermoelectric cooling unit.

\* \* \* \* \*